(12) United States Patent
Xue

(10) Patent No.: US 10,484,248 B2
(45) Date of Patent: Nov. 19, 2019

(54) DATA DECISION METHOD, APPARATUS AND SYSTEM

(71) Applicant: Huawei Technologies Co., Ltd., Shenzhen (CN)

(72) Inventor: Xijun Xue, Beijing (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 197 days.

(21) Appl. No.: 15/596,862

(22) Filed: May 16, 2017

(65) Prior Publication Data

US 2017/0250872 A1  Aug. 31, 2017

Related U.S. Application Data

(63) Continuation of application No. PCT/CN2015/092951, filed on Oct. 27, 2015.

(30) Foreign Application Priority Data

Mar. 24, 2015  (CN) .......................... 2015 1 0130374

(51) Int. Cl.
*G06F 15/173* (2006.01)
*H04L 12/24* (2006.01)
(Continued)

(52) U.S. Cl.
CPC ............ *H04L 41/14* (2013.01); *G06F 16/951* (2019.01); *H04L 67/10* (2013.01); *H04L 67/12* (2013.01); *H04W 88/16* (2013.01)

(58) Field of Classification Search
CPC ................................. H04L 41/14; H04L 67/12
See application file for complete search history.

(56) References Cited

U.S. PATENT DOCUMENTS

2004/0122708 A1  6/2004 Avinash et al.
2006/0136292 A1*  6/2006 Bhati ..................... G06Q 30/02
 705/14.41
(Continued)

FOREIGN PATENT DOCUMENTS

CN  1751309 A  3/2006
CN  101131624 A  2/2008
(Continued)

OTHER PUBLICATIONS

Machine Translation and Abstract of Chinese Publication No. CN101131624, Feb. 27, 2008, 38 pages.
(Continued)

*Primary Examiner* — Hua Fan
(74) *Attorney, Agent, or Firm* — Conley Rose, P.C.

(57) ABSTRACT

A data decision method, apparatus and system relate to the field of communications technologies, where they accurately and effectively analyze information included in fragmented data. The method includes obtaining, by a data decision apparatus, analysis conditions for data analysis, reporting, by the data decision apparatus, the analysis conditions to a cloud server such that the cloud server determines, according to the analysis conditions, a first data type that the data decision apparatus can process, obtaining, by the data decision apparatus, first data satisfying the first data type, where the first data is perception data generated by a human body device, performing, by the data decision apparatus, data analysis and data decision on the first data, and generating first decision data, where the first decision data is decision information of a data characteristic reflected for the first data.

22 Claims, 6 Drawing Sheets

(51) Int. Cl.
*G06F 16/951* (2019.01)
*H04L 29/08* (2006.01)
*H04W 88/16* (2009.01)

(56) References Cited

U.S. PATENT DOCUMENTS

| | | | |
|---|---|---|---|
| 2011/0093619 A1* | 4/2011 | Nelson | G06Q 10/06 709/248 |
| 2013/0042008 A1 | 2/2013 | Das et al. | |

FOREIGN PATENT DOCUMENTS

| | | |
|---|---|---|
| CN | 101135953 A | 3/2008 |
| CN | 101741892 A | 6/2010 |
| CN | 102065112 A | 5/2011 |
| CN | 102281314 A | 12/2011 |
| CN | 102946415 A | 2/2013 |

OTHER PUBLICATIONS

Machine Translation and Abstract of Chinese Publication No. CN101135953, Mar. 5, 2008, 37 pages.
Machine Translation and Abstract of Chinese Publication No. CN102281314, Dec. 14, 2011, 17 pages.
Machine Translation and Abstract of Chinese Publication No. CN102946415, Feb. 27, 2013, 19 pages.
Foreign Communication From a Counterpart Application, Chinese Application No. 201510130374.X, Chinese Office Action dated Oct. 31, 2018, 6 pages.
Machine Translation and Abstract of Chinese Publication No. CN101741892, Jun. 16, 2010, 10 pages.
Machine Translation and Abstract of Chinese Publication No. CN102065112, May 18, 2011, 20 pages.
Foreign Communication From a Counterpart Application, PCT Application No. PCT/CN2015/092951, English Translation of International Search Report dated Jan. 27, 2016, 2 pages.

* cited by examiner

DATA DECISION METHOD, APPARATUS AND SYSTEM

CROSS-REFERENCE TO RELATED APPLICATIONS

This application is a continuation of International Patent Application No. PCT/CN2015/092951 filed on Oct. 27, 2015, which claims priority to Chinese Patent Application No. 201510130374.X, filed on Mar. 24, 2015. The disclosures of the aforementioned applications are hereby incorporated by reference in their entireties.

TECHNICAL FIELD

The present disclosure relates to the field of communications technologies, and in particular, to a data decision method, apparatus and system.

BACKGROUND

Currently, a large quantity of wearable devices, such as a smart band and implantable devices, such as a heart pacemaker have been widely applied to the daily life of users. These human body devices (a wearable device and an implantable device are collectively referred to as human body devices in this application) may sense a human body activity and parameters of an external environment, and the human body devices may summarize obtained data such that users can properly arrange various matters in the life according to the data provided by the human body devices.

However, with emergence of human body devices in a large quantity, each person may possess multiple human body devices at the same time, and therefore, how to perform effective analysis according to data provided by the multiple human body devices becomes a problem to be resolved urgently. For example, after a user tumbles, a gesture detector on the body of the user obtains gesture change data, a blood pressure monitor obtains blood pressure change data, and a heart rate monitor obtains heart rate change data. In this application, data generated by human body devices is collectively referred to as perception data. It can be seen that, the perception data obtained by these human body devices is fragmented, and a relatively accurate data analysis result cannot be provided to the user according to the fragmented data.

SUMMARY

Embodiments of the present disclosure provide a data decision method, apparatus and system in order to accurately and effectively analyze information included in fragmented data.

According to a first aspect, an embodiment of the present disclosure provides a data decision method, including obtaining, by a data decision apparatus, analysis conditions for data analysis, where the analysis conditions refer to storage space information and computing rate information of the data decision apparatus and information about a communication rate between the data decision apparatus and a cloud server, where the cloud server is connected to the data decision apparatus, reporting, by the data decision apparatus, the analysis conditions to the cloud server such that the cloud server determines, according to the analysis conditions, a first data type that the data decision apparatus can process, obtaining, by the data decision apparatus, first data satisfying the first data type, where the first data is perception data generated by a human body device connected to the data decision apparatus, performing, by the data decision apparatus, data analysis and data decision on the first data, and generating first decision data, where the first decision data is decision information of a data characteristic reflected for the first data.

With reference to the first aspect, in a first possible implementation manner of the first aspect, after reporting, by the data decision apparatus, the analysis conditions to the cloud server, the method further includes determining, by the data decision apparatus, a second data type according to the analysis conditions, sending, by the data decision apparatus, the second data type to the cloud server such that the cloud server determines, according to the analysis conditions, whether the data decision apparatus has a capability to process the second data type, and obtaining, by the data decision apparatus, first data satisfying the first data type or the second data type when the data decision apparatus receives a message that the cloud server allows the data decision apparatus to process data of the second data type.

With reference to the first possible implementation manner of the first aspect, in a second possible implementation manner of the first aspect, before sending, by the data decision apparatus, the second data type to the cloud server, the method further includes determining, by the data decision apparatus, whether the first data type is consistent with the second data type, and sending, by the data decision apparatus, the second data type to the cloud server such that the cloud server determines, according to the analysis conditions, whether the data decision apparatus has the capability to process the second data type when the first data type is inconsistent with the second data type.

With reference to the first aspect, in a third possible implementation manner of the first aspect, when second data that does not satisfy the first data type is received, sending, by the data decision apparatus, the second data to the cloud server such that the cloud server performs data analysis according to the second data in order to obtain an analysis result for the second data.

With reference to the third possible implementation manner of the first aspect, in a fourth possible implementation manner of the first aspect, after performing, by the data decision apparatus, data analysis and data decision on the first data, and generating first decision data, the method further includes sending, by the data decision apparatus, the first decision data to the cloud server such that the cloud server modifies the first decision data according to the analysis result for the second data, and obtains second decision data after the modification, where the second decision data is decision information of a data characteristic reflected for the second data and the first decision data.

With reference to the third possible implementation manner of the first aspect, in a fifth possible implementation manner of the first aspect, after performing, by the data decision apparatus, data analysis and data decision on the first data, and generating first decision data, the method further includes sending, by the data decision apparatus, the first data and the first decision data to the cloud server such that the cloud server modifies the first decision data according to the first data and the second data, and obtains third decision data after the modification, where the third decision data is decision information of a data characteristic reflected for the first data and the second data.

According to a second aspect, an embodiment of the present disclosure provides a data decision method, including receiving, by a cloud server, analysis conditions for data analysis that are sent by a data decision apparatus, where the analysis conditions refer to storage space information and computing rate information of the data decision apparatus and information about a communication rate between the data decision apparatus and the cloud server, where the cloud server is connected to the data decision apparatus, and determining, by the cloud server according to the analysis conditions, a first data type that the data decision apparatus can process such that the data decision apparatus performs data analysis and data decision on first data satisfying the first data type, and generates first decision data.

With reference to the second aspect, in a first possible implementation manner of the second aspect, after receiving, by a cloud server, analysis conditions for data analysis sent by a data decision apparatus, the method further includes receiving, by the cloud server, a second data type sent by the data decision apparatus, where the second data type is determined by the data decision apparatus according to the analysis conditions, and sending, to the data decision apparatus, a message for allowing the data decision apparatus to process data of the second data type if the cloud server determines according to the analysis conditions that the data decision apparatus has a capability to process the second data type such that the data decision apparatus obtains first data satisfying the first data type or the second data type.

With reference to the second aspect, in a second possible implementation manner of the second aspect, after the receiving, by a cloud server, analysis conditions for data analysis that are sent by a data decision apparatus, the method further includes receiving, by the cloud server, second data and the first decision data that are sent by the data decision apparatus, where the second data refers to perception data that does not satisfy the first data type, performing, by the cloud server, data analysis according to the second data in order to obtain an analysis result for the second data, and modifying, by the cloud server, the first decision data according to the analysis result for the second data, and obtaining first decision data after the modification.

With reference to the second possible implementation manner of the second aspect, in a third possible implementation manner of the second aspect, the cloud server further receives the first data sent by the data decision apparatus, where modifying, by the cloud server, the first decision data according to the analysis result for the second data, and obtaining second decision data after the modification includes modifying, by the cloud server, the first decision data according to the first data and the analysis result for the second data, and obtaining first decision data after the modification.

With reference to any one of the second aspect or the first to third possible implementation manners of the second aspect, in a fourth possible implementation manner of the second aspect, the method further includes obtaining, by the cloud server, perception data sent by a first gateway, where the first gateway refers to any gateway except the data decision apparatus, and modifying, by the cloud server, the first decision data according to the perception data obtained by the first gateway.

According to a third aspect, an embodiment of the present disclosure provides a data decision apparatus, including an obtaining unit configured to obtain analysis conditions for data analysis, where the analysis conditions refer to storage space information and computing rate information of the data decision apparatus and information about a communication rate between the data decision apparatus and a cloud server, where the cloud server is connected to the data decision apparatus, and obtain first data satisfying the first data type, where the first data is perception data generated by a human body device connected to the data decision apparatus, a sending unit configured to report the analysis conditions in the obtaining unit to the cloud server such that the cloud server determines, according to the analysis conditions, the first data type that the data decision apparatus can process, and a data decision unit configured to perform data analysis and data decision on the first data in the obtaining unit, and generate first decision data, where the first decision data is decision information of a data characteristic reflected for the first data.

With reference to the third aspect, in a first possible implementation manner of the third aspect, the data decision apparatus further includes a determining unit, where the determining unit is configured to determine a second data type according to the analysis conditions in the obtaining unit. The sending unit is further configured to send the second data type in the determining unit to the cloud server such that the cloud server determines, according to the analysis conditions, whether the data decision apparatus has a capability to process the second data type, and the obtaining unit is further configured to obtain first data satisfying the first data type or the second data type when a message that the cloud server allows the data decision apparatus to process data of the second data type is received.

With reference to the first possible implementation manner of the third aspect, in a second possible implementation manner of the third aspect, the determining unit is further configured to determine whether the first data type is consistent with the second data type, and the sending unit is further configured to send the second data type to the cloud server such that the cloud server determines, according to the analysis conditions, whether the data decision apparatus has the capability to process the second data type when the first data type is inconsistent with the second data type in the determining unit.

With reference to the third aspect, in a third possible implementation manner of the third aspect, the sending unit is further configured to send the second data to the cloud server such that the cloud server performs data analysis according to the second data in order to obtain an analysis result for the second data when second data that does not satisfy the first data type is received.

With reference to the third possible implementation manner of the third aspect, in a fourth possible implementation manner of the third aspect, the sending unit is further configured to send the first decision data to the cloud server such that the cloud server modifies the first decision data according to the analysis result for the second data, and obtains second decision data after the modification, where the second decision data is decision information of a data characteristic reflected for the second data and the first decision data.

With reference to the third possible implementation manner of the third aspect, in a fifth possible implementation manner of the third aspect, the sending unit is further configured to send the first data and the first decision data to the cloud server such that the cloud server modifies the first decision data according to the first data and the second data, and obtains third decision data after the modification, where the third decision data is decision information of a data characteristic reflected for the first data and the second data.

According to a fourth aspect, an embodiment of the present disclosure provides a cloud server, including a receiving unit configured to receive analysis conditions for data analysis that are sent by a data decision apparatus, where the analysis conditions refer to storage space information and computing rate information of the data decision apparatus and information about a communication rate between the data decision apparatus and the cloud server, where the cloud server is connected to the data decision apparatus, and a determining unit configured to determine, according to the analysis conditions in the receiving unit, a first data type that the data decision apparatus can process such that the data decision apparatus performs data analysis and data decision on first data satisfying the first data type, and generates first decision data.

With reference to the fourth aspect, in a first possible implementation manner of the fourth aspect, the cloud server further includes a sending unit, where the receiving unit is further configured to receive a second data type sent by the data decision apparatus, where the second data type is determined by the data decision apparatus according to the analysis conditions, and the sending unit is configured to send, to the data decision apparatus, a message for allowing the data decision apparatus to process data of the second data type such that the data decision apparatus obtains first data satisfying the first data type or the second data type if the cloud server determines according to the analysis conditions that the data decision apparatus has a capability to process the second data type.

With reference to the fourth aspect, in a second possible implementation manner of the fourth aspect, the cloud server further includes a data processing unit, where the receiving unit is further configured to receive second data and the first decision data that are sent by the data decision apparatus, where the second data refers to perception data that does not satisfy the first data type, and the data processing unit is configured to perform data analysis according to the second data in the receiving unit in order to obtain an analysis result for the second data, and modify the first decision data according to the analysis result for the second data, and obtain first decision data after the modification.

With reference to the second possible implementation manner of the fourth aspect, in a third possible implementation manner of the fourth aspect, the receiving unit is further configured to receive the first data sent by the data decision apparatus, and the data processing unit is further configured to modify the first decision data according to the first data and the analysis result for the second data, and obtain first decision data after the modification.

With reference to any one of the fourth aspect or the first to third possible implementation manners of the fourth aspect, in a fourth possible implementation manner of the fourth aspect, the receiving unit is further configured to obtain perception data sent by a first gateway, where the first gateway refers to any gateway except the data decision apparatus, and the data processing unit is further configured to modify the first decision data according to the perception data that is obtained by the first gateway and that is in the receiving unit.

According to a fifth aspect, an embodiment of the present disclosure provides a data decision system, where the system includes the data decision apparatus according to any one of the third aspect or the first to fifth possible implementation manners of the third aspect, and the cloud server according to any one of the fourth aspect or the first to fourth possible implementation manners of the fourth aspect connected to the data decision apparatus.

With reference to the fifth aspect, in a first possible implementation manner of the fifth aspect, the system further includes a first gateway, and the first gateway is any gateway except the data decision apparatus, where the first gateway is configured to send perception data obtained by the first gateway to the cloud server.

The embodiments of the present disclosure provide a data decision method, apparatus and system, where the data decision apparatus obtains analysis conditions for data analysis, and then reports the analysis conditions to a cloud server in order to determine a first data type that can be processed, where when the data decision apparatus obtains first data satisfying the first data type, the first data is perception data generated by a human body device connected to the data decision apparatus, and performs data analysis and data decision on the first data, and generates first decision data, where the first decision data is decision information of a data characteristic reflected for the first data. It can be seen that, the data decision apparatus may perform rapid and relatively accurate data analysis and decision on various perception data satisfying the first data type, and then may feedback the obtained first decision data to the human body device and a user at first time, thereby resolving, to an extent, a problem that information included in fragmented data cannot be accurately and effectively analyzed, and improving analysis quality for the perception data.

BRIEF DESCRIPTION OF DRAWINGS

To describe the technical solutions in the embodiments of the present disclosure more clearly, the following briefly introduces the accompanying drawings required for describing the embodiments. The accompanying drawings in the following description show merely some embodiments of the present disclosure, and a person of ordinary skill in the art may still derive other drawings from these accompanying drawings without creative efforts.

DESCRIPTION OF EMBODIMENTS

In the following description, to illustrate but not to limit, specific details such as a particular system structure, an interface, and a technology are provided to make a thorough understanding of the present disclosure. However, a person skilled in the art should know that the present disclosure may be practiced in other embodiments without these specific details. In other cases, detailed descriptions of well-known apparatuses, circuits, and methods are omitted such that the present disclosure is described without being obscured by unnecessary details.

A data decision apparatus involved in embodiments of the present disclosure may obtain perception data of each human body device from each human body device possessed by a user, such as a blood pressure value of the user generated by a blood pressure monitor, or video information generated by smart glasses, and the data decision apparatus may serve as a gateway and send the perception data of the human body device to a cloud server such that the cloud server may perform data analysis according to each piece of perception data, and finally obtain decision data according to an analysis result and feedback the decision data to the user and each human body device. Additionally, the data decision apparatus may further perform, to an extent, data analysis and data decision on the perception data generated by each human body device. In the embodiments of the present disclosure, a process in which the data decision apparatus performs data analysis is referred to as lightweight data analysis, and a process in which the cloud server performs data analysis is referred to as comprehensive data analysis. It can be seen that, by performing effective coordination and cooperation between the data decision apparatus and the cloud server on the lightweight data analysis and the comprehensive data analysis, perception data generated by each human body device possessed by a user may be rapidly and accurately analyzed, thereby improving analysis quality for the perception data.

Further, before coordination is performed between the data decision apparatus and the cloud server on the lightweight data analysis and the comprehensive data analysis, the data decision apparatus needs to determine in advance perception data on which the lightweight data analysis needs to be performed by the data decision apparatus, and perception data that needs to be sent by the data decision apparatus to the cloud server such that the cloud server performs the comprehensive data analysis.

Figure 1:
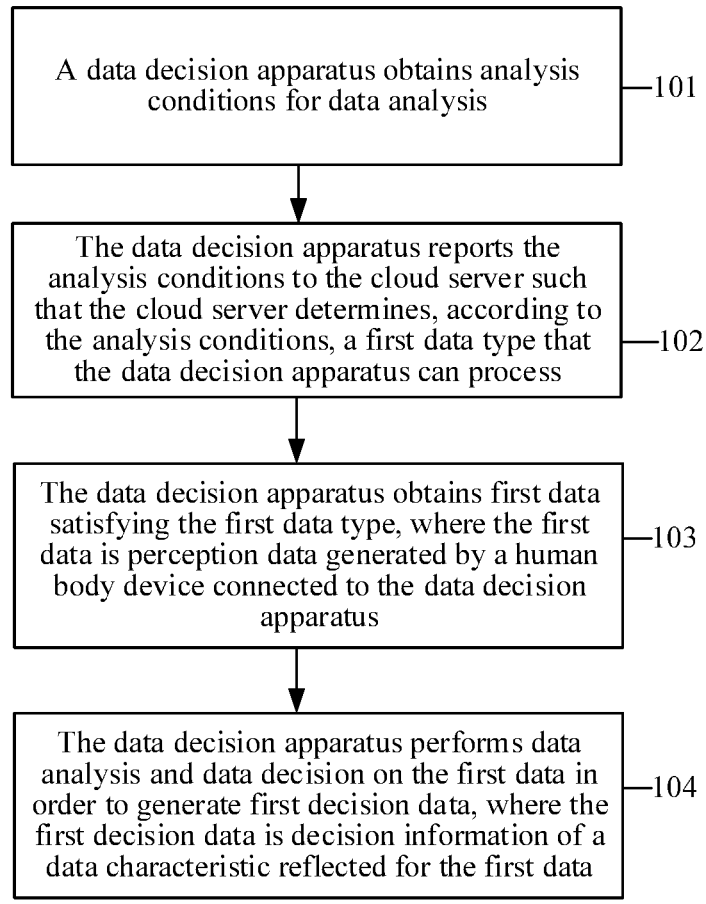
FIG. 1 is a schematic flowchart of a data decision method according to an embodiment of the present disclosure.

Exemplarily, FIG. 1 shows a data decision method provided in an embodiment of the present disclosure, and the method include the following steps.

Step 101: A data decision apparatus obtains analysis conditions for data analysis, where the analysis conditions refer to storage space information and computing rate information of the data decision apparatus and information about a communication rate between the data decision apparatus and a cloud server, where the cloud server is connected to the data decision apparatus.

Step 102: The data decision apparatus reports the analysis conditions to the cloud server such that the cloud server determines, according to the analysis conditions, a first data type that the data decision apparatus can process.

Step 103: The data decision apparatus obtains first data satisfying the first data type, where the first data is perception data generated by a human body device connected to the data decision apparatus.

Step 104: The data decision apparatus performs data analysis and data decision on the first data in order to generate first decision data, where the first decision data is decision information of a data characteristic reflected for the first data.

In step 101, the data decision apparatus first obtains analysis conditions for the data decision apparatus to perform data analysis, where the analysis conditions may include storage space information and computing rate information of the data decision apparatus and information about a communication rate between the data decision apparatus and the cloud server, where the storage space information may include a storage capacity that the data decision apparatus may currently use, the computing rate information may include a load value that the data decision apparatus may use, a resource occupation ratio of the data decision apparatus, a dominant frequency parameter of the data decision apparatus or the like, and the communication rate information may include an available communication rate between the data decision apparatus and the cloud server or the like.

It can be seen that, the storage space information and the computing rate information of the data decision apparatus and the information about the communication rate between the data decision apparatus and the cloud server are main factors that restrict data exchange performed between the data decision apparatus and the cloud server, and therefore, before data exchange is performed between the data decision apparatus and the cloud server, the data decision apparatus needs to determine the storage space information and the computing rate information of the data decision apparatus and the information about the communication rate between the data decision apparatus and the cloud server. For example, storage space that the data decision apparatus may currently use is 8 gigabytes (GB), the dominant frequency parameter of the data decision apparatus is 500 megahertz (MHz) (where idle resources of the data decision apparatus account for 80%), and the available communication rate between the data decision apparatus and the cloud server is 100 megabits per second (Mbps).

Certainly, these analysis conditions may be stored in the data decision apparatus in advance, or may be sent by the cloud server to the data decision apparatus, which is not limited in the present disclosure.

In step 102, after the foregoing analysis conditions are obtained, the data decision apparatus may report the analysis conditions in step 101 to the cloud server such that the cloud server determines, according to the analysis conditions, the first data type that the data decision apparatus can process, such as a heart rate value generated by a heart rate monitoring apparatus.

Further, the storage space information and the computing rate information of the data decision apparatus and the information about the communication rate between the data decision apparatus and the cloud server are the main factors that restrict data exchange performed between the data decision apparatus and the cloud server, and therefore, when a data analysis task of the first data type satisfies the analysis conditions, for example, if the first data type is a real-time blood pressure value generated by a blood pressure measurer, the data analysis task of the first data type is to compare the real-time blood pressure value with a healthy blood pressure or a healthy blood pressure range, and when the data decision apparatus compares the real-time blood pressure value with the healthy blood pressure or the healthy blood pressure range, if consumed storage space is less than the storage capacity that the data decision apparatus may currently use, a value of an occupied load is less than the load value that is in the computing rate information and that may be used, and the communication rate between the data decision apparatus and the cloud server is less than the available communication rate in the communication rate information in the foregoing analysis conditions (that is, current communication quality of communication between the data decision apparatus and the cloud server is relatively low), it may be determined that the real-time blood pressure value generated by the blood pressure measurer is the first data type that the data decision apparatus can process.

Further, there are two methods for determining whether the data analysis task of the first data type satisfies the analysis conditions. In a first method, the analysis conditions may be sent by the data decision apparatus to the cloud server such that the cloud server determines, according to the analysis conditions, the first data type that the data decision apparatus can process, that is, determines whether the data analysis task of the first data type satisfies the analysis conditions, and sends a data analysis indication of the first data type to the data decision apparatus if the data analysis task of the first data type satisfies the analysis conditions such that the data decision apparatus obtains, according to the data analysis indication, the first data satisfying the first data type.

In a second method, the data decision apparatus may determine, according to the analysis conditions, a second data type that the data decision apparatus can process. For example, the data decision apparatus may search a data analysis model library that is stored in advance for a second data type analysis model corresponding to the second data type, then compare information about storage space occupied by a data analysis task of the second data type, computing rate information and information about a communication rate between the data decision apparatus and the cloud server in the second data type analysis model with the storage space information, the computing rate information and the information about the communication rate between the data decision apparatus and the cloud server in the foregoing analysis conditions, and determine whether the data analysis task of the second data type satisfies the analysis conditions, and determine the second data type is a data type that the data decision apparatus can process, and then send the second data type to the cloud server if the data analysis task of the second data type satisfies the analysis conditions such that the cloud server allows the data decision apparatus to process data of the second data type.

Certainly, before sending the second data type to the cloud server, the data decision apparatus may further determine whether the first data type already sent by the cloud server is consistent with the second data type determined by the data decision apparatus. The data decision apparatus does not need to send the second data type to the cloud server if the first data type is consistent with the second data type, or the data decision apparatus may send the second data type to the cloud server if the first data type is inconsistent with the second data type such that the cloud server allows the data decision apparatus to process data of the second data type.

The data analysis model library may include multiple data analysis models for perception data, such as a data analysis model for heartbeat information generated by a heart pacemaker, and a data analysis model for gesture conversion information generated by a gesture detector. Moreover, the data decision apparatus may further update the data models in the data analysis model library periodically in order to ensure accuracy of the data decision apparatus when determining whether the data analysis task of the first data type satisfies the analysis conditions.

Certainly, the data decision apparatus may further estimate information about storage space occupied when the data analysis task of the first data type is executed, the computing rate information and the information about the communication rate between the data decision apparatus and the cloud server, then compare a result after the estimation with the storage space information, the computing rate information and the information about the communication rate between the data decision apparatus and the cloud server in the foregoing analysis conditions, and finally determine whether the data analysis task of the first data type satisfies the analysis conditions, which is not limited in the present disclosure.

In step 103, the data decision apparatus obtains, according to the first data type determined in step 102, first data satisfying the first data type, where the first data is perception data generated by a human body device connected to the data decision apparatus. For example, if the first data type that is already determined and on which data analysis needs to be performed is a current blood pressure value generated by a blood pressure monitor, when obtaining any blood pressure value generated by the blood pressure monitor (that is, any blood pressure value is the first data), the data decision apparatus may perform data analysis on the first data to obtain an analysis result for the first data.

For example, if the data decision apparatus obtains a current blood pressure value of a user from the blood pressure monitor, because the current blood pressure value is the first data type that is already determined by the data decision apparatus and on which data analysis needs to be performed, that is, the current blood pressure value satisfies the first data type, the data decision apparatus may perform data analysis according to the current blood pressure value, that is, compare the current blood pressure value with the healthy blood pressure range, and obtain an analysis result for the first data, that is, determine whether the current blood pressure value conforms to the healthy blood pressure range.

Further, if in step 102, the data decision apparatus already determines the second data type that the data decision apparatus can process, that is, the data decision apparatus not only can process the first data type, but also can process the second data type, in step 103, the data decision apparatus may obtain the first data satisfying the first data type or the second data type. The first data may be multiple pieces of perception data generated by one or more human body devices.

In step 104, the data decision apparatus performs data analysis on the first data obtained in step 103, then performs data decision according to an analysis result for the first data, and generates first decision data, where the first decision data is decision information of a data characteristic reflected for the first data.

Further, multiple analysis policies of perception data may be stored in the data decision apparatus in advance. For example, a blood glucose value obtained by the data decision apparatus is compared with a healthy blood glucose value stored in the data decision apparatus, to determine whether the blood glucose value obtained by the data decision apparatus is greater than the healthy blood glucose value. In this way, when obtaining the first data, the data decision apparatus may search for an analysis policy associated with the first data, and then perform data analysis on the first data according to the analysis policy in order to obtain an analysis result for the first data.

Correspondingly, if the data obtained by the data decision apparatus from the human body device is not the first data, that is, the data obtained by the data decision apparatus from the human body device does not satisfy the first data type in step 102, and this type of data is referred to as second data in this embodiment of the present disclosure, the data decision apparatus may send the second data to the cloud server, and the cloud server performs data analysis on the second data. In this way, the cloud server and the data decision apparatus may simultaneously perform data analysis on the obtained first data and second data generated by each human body device, thereby improving analysis efficiency for the perception data.

The first data is at least one piece of perception data generated by any human body device, that is, the first data may be multiple pieces of data of one type, and may include multiple pieces of perception data generated by multiple human body devices, and therefore, when obtaining the first data, the data decision apparatus may perform data analysis and data decision on the first data, and generate first decision data, where the first decision data is decision information of a data characteristic jointly reflected for at least one piece of perception data of the first data.

For example, if the first data that is already obtained by the data decision apparatus in step 103 and on which data analysis needs to be performed includes a weight value generated by a weighing scale and a blood pressure value generated by the blood pressure monitor, when obtaining the weight value generated by the weighing scale, the data decision apparatus may perform data analysis on whether the weight value is excessive, and obtain one analysis result for the first data: the weight value is severely excessive. Moreover, when obtaining the blood pressure value generated by the blood pressure monitor, the data decision apparatus may perform data analysis on whether the blood pressure value is in a proper range, and obtain a second analysis result for the first data: the blood pressure value is slightly high. Then, the data decision apparatus may perform data decision on the two analysis results, and provide proper decision information to the user. For example, a severely excessive weight value indicates that body health of the user has a problem, a slightly high blood pressure value also indicates that the body health of the user has a problem, and a severely excessive weight value may cause a slightly high blood pressure value, and therefore, the data decision apparatus generates first decision data for the user according to a data characteristic and an association relationship between analysis results, for example, advises the user to lose weight and pay attention to the body health.

Certainly, a data decision model library may also be stored in the data decision apparatus in advance. Similar to the data analysis model library, the data analysis model library may include data decision models for multiple analysis results, for example, a data decision model for analysis results for a blood pressure value and a blood glucose value, for example, ranges in which changes in relative values of the blood pressure value and the blood glucose value are normal, and ranges in which changes in the relative values of the blood pressure value and the blood glucose value are abnormal, and for another example, a data decision model for analysis results for gesture change data and a heart rate value. For example, the analysis result for the gesture change data indicates that the user is in a violent exercise state, and if the analysis result for the heart rate value indicates that a heart rate of the user increases, it is a normal phenomenon.

So far, it can be seen that, the data decision apparatus may perform data exchange with the cloud server for multiple pieces of obtained perception data, determine, according to analysis conditions for the data decision apparatus to perform data analysis, to perform data analysis on some perception data (that is, the first data), and generate first decision data according to multiple analysis results for the first data in order to feedback the first decision data to the user at first time, thereby improving analysis efficiency for the perception data in an application scenario of multiple human body devices.

Figure 2:
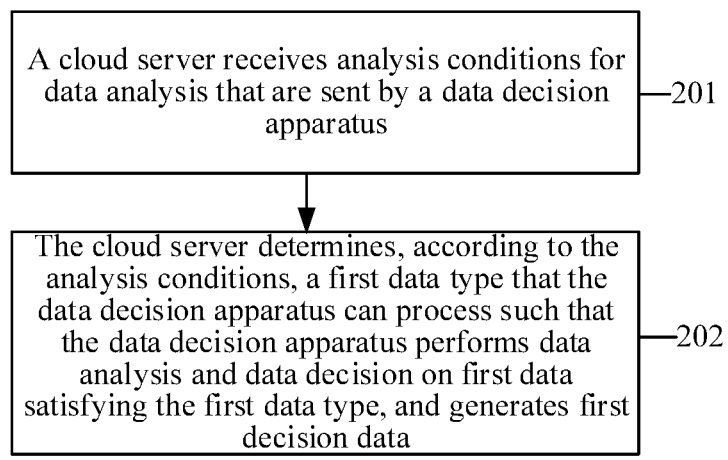
FIG. 2 is a schematic flowchart of a data decision method according to an embodiment of the present disclosure.

In another possible implementation manner of the embodiments of the present disclosure, a cloud server may determine, according to received analysis conditions, a first data type that a data decision apparatus can process. Exemplarily, FIG. 2 shows a data decision method provided in an embodiment of the present disclosure, and method includes the following steps.

Step 201: A cloud server receives analysis conditions for data analysis that are sent by a data decision apparatus, where the analysis conditions refer to storage space information and computing rate information of the data decision apparatus and information about a communication rate between the data decision apparatus and the cloud server.

Step 202: The cloud server determines, according to the analysis conditions, a first data type that the data decision apparatus can process such that the data decision apparatus performs data analysis and data decision on first data satisfying the first data type, and generates first decision data.

The cloud server and the data decision apparatus complete, by means of data exchange, analysis and decision on multiple pieces of obtained perception data generated by human body devices, where the data decision apparatus may serve as a gateway of the human body devices and obtain multiple pieces of perception data generated by the human body devices. Moreover, the data decision apparatus may further perform lightweight data analysis on some of the obtained perception data, and the cloud server may perform comprehensive data analysis on the obtained perception data. It can be seen that, by performing effective coordination and cooperation between the data decision apparatus and the cloud server on the lightweight data analysis and the comprehensive data analysis, perception data generated by each human body device possessed by a user may be rapidly and accurately analyzed, thereby improving analysis quality for the perception data.

In step 201, after obtaining the analysis conditions for the data decision apparatus to perform data analysis, the data decision apparatus sends the analysis conditions to the cloud server, where the analysis conditions refer to storage space information and computing rate information of the data decision apparatus, information about a communication rate between the data decision apparatus and the cloud server, and the like.

The storage space information and the computing rate information of the data decision apparatus, and the information about the communication rate between the data decision apparatus and the cloud server are main factors that restrict data exchange performed between the data decision apparatus and the cloud server, and therefore, the cloud server may determine, according to the analysis conditions, perception data on which lightweight data analysis needs to be performed by the data decision apparatus, and perception data that needs to be sent by the data decision apparatus to the cloud server such that the cloud server performs comprehensive data analysis.

In step 202, after obtaining the analysis conditions for data analysis in step 201, the cloud server may determine according to the analysis conditions that the data decision apparatus performs data analysis and data decision on the first data type, where a data analysis task of the first data type satisfies the analysis conditions.

Further, the cloud server may actively determine, according to the analysis conditions obtained in step 201, the first data type on which data analysis needs to be performed by the data decision apparatus, and send the first data type to the data decision apparatus in order to instruct the data decision apparatus to perform data analysis and data decision on data satisfying the first data type.

Alternatively, the cloud server may determine, according to a second data type actively sent by the data decision apparatus, whether the data decision apparatus has a capability to process the second data type, and if the data decision apparatus has a capability to process the second data type, the cloud server sends, to the data decision apparatus, a message for allowing the data decision apparatus to process data of the second data type such that the data decision apparatus obtains the first data satisfying the first data type or the second data type.

Exemplarily, the present disclosure provides two methods for the cloud server to instruct the data decision apparatus to perform data analysis on the first data satisfying the first data type or the second data type, where the methods are as follows.

In a method 1, after the data decision apparatus obtains the foregoing analysis conditions, the cloud server may actively determine, according to the foregoing analysis conditions, the first data type on which data analysis needs to be performed by the data decision apparatus. Similarly, the cloud server may search for a first data type analysis model corresponding to the first data type, then compare the information about occupied storage space, the computing rate information and the information about the communication rate between the data decision apparatus and the cloud server in the first data type analysis model with the storage space information, the computing rate information and the information about the communication rate between the data decision apparatus and the cloud server in the foregoing analysis conditions, and determine whether the data analysis task of the first data type satisfies the analysis conditions. The cloud server sends a data analysis indication for the first data type to the data decision apparatus in order to instruct the data decision apparatus to perform data analysis on data satisfying the first data type if the data analysis task of the first data type satisfies the analysis conditions.

In a method 2, after the data decision apparatus obtains the foregoing analysis conditions, the data decision apparatus determines, according to the analysis conditions, the second data type on which data analysis needs to be performed, and for a specific method, reference may be made to step 102. In this case, the data decision apparatus generates a data analysis request, where the data analysis request is used to request the cloud server to allow to perform data analysis on data satisfying the second data type. In this way, after receiving the data analysis request sent by the data decision apparatus, the cloud server may determine, according to the analysis conditions, whether to approve the data analysis request sent by the data decision apparatus.

Further, the cloud server may calculate, according to the data analysis request, whether a data analysis task of the second data type satisfies the analysis conditions obtained in step 201. For example, a data analysis model library is stored in the cloud server. Therefore, the cloud server may search for a second data type analysis model corresponding to the second data type, then compare the information about storage space occupied by the data analysis task of the second data type, the computing rate information and the information about the communication rate between the data decision apparatus and the cloud server in the second data type analysis model with the storage space information, the computing rate information and the information about the communication rate between the data decision apparatus and the cloud server in the foregoing analysis conditions, and determine whether the data analysis task of the second data type satisfies the analysis conditions. If the data analysis task of the second data type satisfies the analysis conditions, the cloud server sends a data analysis allowance response to the data decision apparatus in order to allow the data decision apparatus to process data satisfying the second data type.

So far, the cloud server determines according to the analysis conditions obtained in step 201 that the data decision apparatus performs data analysis and data decision on the first data satisfying the first data type or the second data type.

It can be seen that, using step 202, the cloud server may indicate, to the data decision apparatus, multiple data analysis tasks of the first data type that satisfy the foregoing analysis conditions. In this way, when the data decision apparatus receiving multiple pieces of perception data generated by multiple human body devices possessed by a user, the data decision apparatus may perform data analysis on the first data according to the data analysis tasks of the first data that are indicated by the cloud server, and then obtain an analysis result for the first data.

After the data decision apparatus obtains multiple analysis results for the first data, the data decision apparatus may perform data decision on the multiple analysis results for the first data, and obtain the first decision data. However, in the first decision data obtained by the data decision apparatus, only some perception data determined by the storage space information and the computing rate information of the data decision apparatus and the information about the communication rate between the data decision apparatus and the cloud server is considered. When multiple pieces of perception data obtained by the data decision apparatus include second data, where the second data is data that does not satisfy the first data type or the second data type, the data decision apparatus cannot perform data analysis on the second data, and therefore, the first decision data obtained by the data decision apparatus is not all-around.

Therefore, after obtaining the second data, the data decision apparatus sends the second data to the cloud server such that the cloud server performs data analysis on the second data in order to obtain an analysis result for the second data. Further, the data decision apparatus sends the obtained first decision data to the cloud server. In this way, the cloud server may modify the first decision data according to the analysis result for the second data, and obtain second decision data after the modification.

An example in which the first data includes a weight value generated by a weighing scale and a blood pressure value generated by a blood pressure monitor in step 104 is still used, and the first decision data generated by the data decision apparatus advise the user to lose weight and pay attention to body healthy. Moreover, besides obtaining the first data, the data decision apparatus further obtains the second data. For example, the second data is exercise data of the user in one month provided by a smart band of the user. Then, the data decision apparatus sends the second data to the cloud server, and the cloud server performs analysis on the second data, and determines that an exercise amount of the user in one month is severely low. Then, the cloud server may modify the first decision data sent by the data decision apparatus, and generate the second decision data, for example, to advise the user to increase exercise and the like on the basis of advising the user to lose weight and pay attention to body healthy.

Certainly, a data decision model library may also be stored in the cloud server in advance. Similar to the data analysis model library, the data decision model library may include data decision models for multiple analysis results, for details, reference may be made to step 104, and the cloud server may modify the first decision data according to a data decision model.

Additionally, the cloud server may also directly obtain, from the data decision apparatus, the perception data, that is, the first data and the second data generated by the human body devices possessed by the user, and perform analysis and decision on the perception data, and finally generate third decision data. For example, after the data decision apparatus obtains perception data generated by multiple human body devices, if a current communication rate between the data decision apparatus and the cloud server is greater than a threshold, the data decision apparatus may send all of the obtained perception data to the cloud server such that the cloud server performs data analysis and decision on the perception data, and obtain the third decision data.

It can be seen that, compared with the second decision data and the third decision data, information in the first decision data may be not all-around. However, when generating the first decision data, the data decision apparatus does not need to perform interaction with the cloud server. Therefore, data analysis and decision efficiency is greatly improved, relatively accurate decision data may be rapidly provided to the user, and by means of modification performed by the cloud server on the first decision data, more accurate decision data may be provided to the user.

This embodiment of the present disclosure provides a data decision method, where a data decision apparatus obtains analysis conditions for data analysis, and then reports the analysis conditions to a cloud server in order to determine a first data type that can be processed, where when the data decision apparatus obtains first data satisfying the first data type, the first data is perception data generated by a human body device connected to the data decision apparatus, and performs data analysis and data decision on the first data, and generates first decision data, where the first decision data is decision information of a data characteristic reflected for the first data. It can be seen that, the data decision apparatus may perform rapid and relatively accurate data analysis and decision on various perception data satisfying the first data type, and then may feedback the obtained first decision data to the human body device and a user at first time, thereby resolving, to an extent, a problem that multiple human body devices cannot effectively coordinate to separately perceive the perception data, and improving analysis quality for the perception data.

Figure 3:
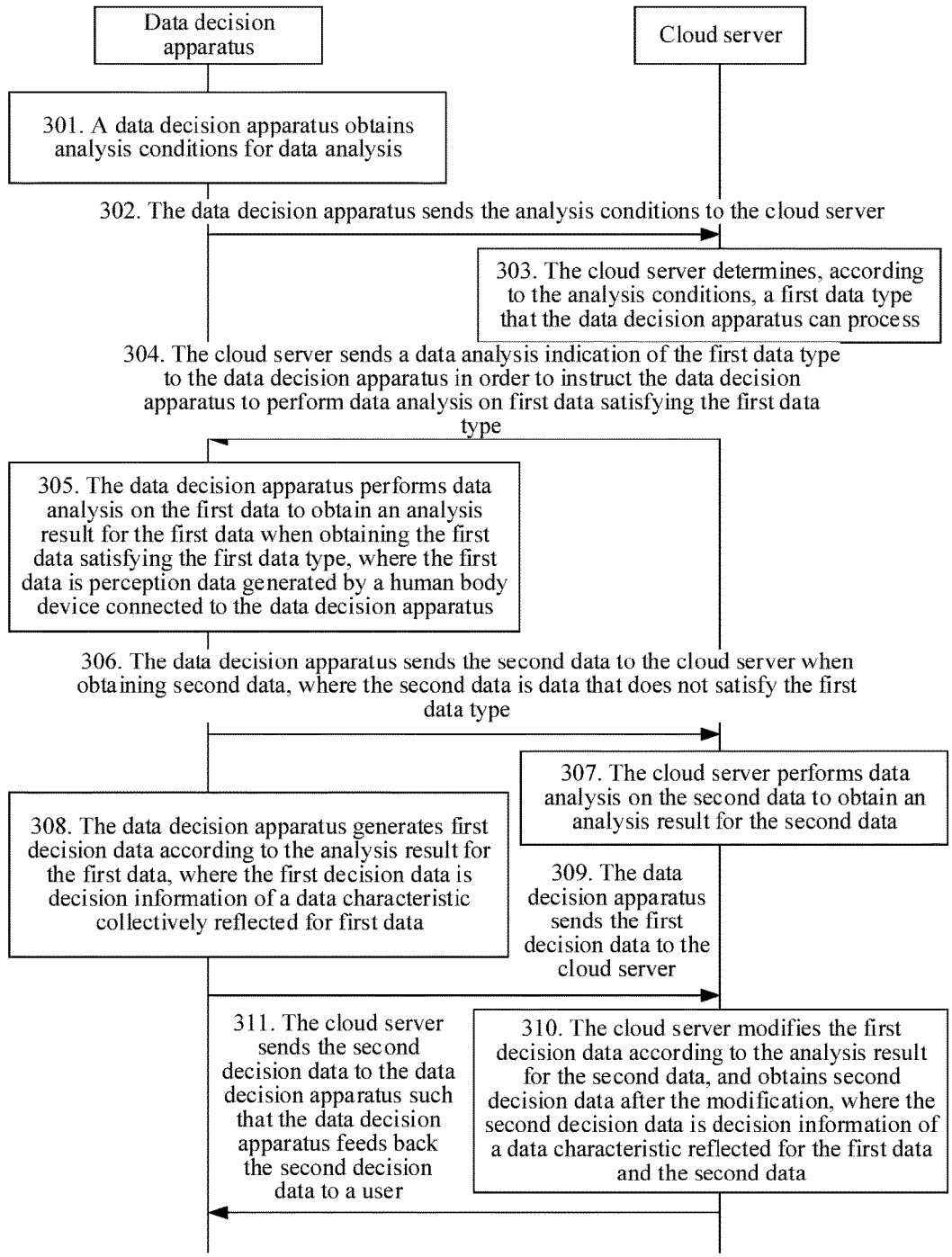
FIG. 3 is a schematic interaction diagram of a data decision method according to an embodiment of the present disclosure.

A data decision apparatus may be connected to multiple human body devices. The data decision apparatus may perform data exchange with a cloud server when receiving perception data generated by any human body device in order to perform data analysis and data decision on perception data generated by each human body device, and finally, accurate decision data is provided to a user rapidly. To satisfy such a requirement, as shown in FIG. 3, an embodiment of the present disclosure provides a data decision method, and the method includes the following steps.

Step 301: A data decision apparatus obtains analysis conditions for data analysis, where the analysis conditions refer to storage space information and computing rate information of the data decision apparatus and information about a communication rate between the data decision apparatus and a cloud server.

Step 302: The data decision apparatus sends the analysis conditions to the cloud server.

Step 303: The cloud server determines, according to the analysis conditions, a first data type that the data decision apparatus can process.

Step 304: The cloud server sends a data analysis indication of the first data type to the data decision apparatus in order to instruct the data decision apparatus to perform data analysis on first data satisfying the first data type.

Step 305: The data decision apparatus performs data analysis on the first data to obtain an analysis result for the first data when obtaining the first data satisfying the first data type, where the first data is perception data generated by a human body device connected to the data decision apparatus.

Step 306: The data decision apparatus sends the second data to the cloud server when obtaining second data, where the second data is data that does not satisfy the first data type.

Step 307: The cloud server performs data analysis on the second data to obtain an analysis result for the second data.

Step 308: The data decision apparatus generates first decision data according to the analysis result for the first data, where the first decision data is decision information of a data characteristic collectively reflected for the first data.

Step 309: The data decision apparatus sends the first decision data to the cloud server.

Step 310: The cloud server modifies the first decision data according to the analysis result for the second data, and obtains second decision data after the modification, where the second decision data is decision information of a data characteristic reflected for the first data and the second data.

Step 311: The cloud server sends the second decision data to the data decision apparatus such that the data decision apparatus feeds back the second decision data to a user.

In step 301, the storage space information and the computing rate information of the data decision apparatus and the information about the communication rate between the data decision apparatus and the cloud server are main factors that restrict data exchange performed between the data decision apparatus and the cloud server, and therefore, before data exchange is performed between the data decision apparatus and the cloud server, the data decision apparatus needs to determine the storage space information and the computing rate information of the data decision apparatus and the information about the communication rate between the data decision apparatus and the cloud server. For example, storage space that the data decision apparatus may currently use is 8 GB, the dominant frequency parameter of the data decision apparatus is 500 MHz (where idle resources of the data decision apparatus account for 80%), and the available communication rate between the data decision apparatus and the cloud server is 100 Mbps.

In step 302, after the foregoing analysis conditions are obtained, to determine perception data on which the data decision apparatus needs to perform lightweight data analysis, and perception data that the data decision apparatus needs to send to the cloud server such that the cloud server performs comprehensive data analysis, the data decision apparatus sends the analysis conditions to the cloud server.

In step 303, after receiving the analysis conditions sent by the data decision apparatus, the cloud server determines, according to the analysis conditions, the first data type that the data decision apparatus can process.

For details, reference may be made to step 102 and step 202, and exemplary description is performed herein using an example in which the first data type is a blood pressure value generated by a blood pressure monitor. After receiving the analysis conditions, the cloud server determines a data analysis task of the first data type, that is, to compare the blood pressure value with a healthy blood pressure range, to determine whether the blood pressure value conforms to the analysis conditions. For example, in the analysis conditions, the storage space that the data decision apparatus may currently use is 8 GB, the dominant frequency parameter of the data decision apparatus is 500 MHz (where idle resources of the data decision apparatus account for 80%), and the available communication rate between the data decision apparatus and the cloud server is 100 Mbps. Moreover, when the data analysis task of the first data type is performed, storage space of 500 megabytes (MB) is needed, and a dominant frequency parameter of 80 Mbps is needed (10% of the idle resources need to be occupied), which both satisfy various conditions of the analysis conditions. Therefore, the cloud server may determine that the data decision apparatus can perform data analysis on the first data type, that is, determine that the first data type that the data decision apparatus can process is the blood pressure value generated by the blood pressure monitor.

Alternatively, after receiving the analysis conditions, the cloud server searches for historical data that is already stored, and then finds that the data decision apparatus once processes a data analysis task for the blood pressure value, and therefore, the cloud server may determine that the data decision apparatus performs data analysis on the first data type, that is, the blood pressure value.

In step 304, after determining that the data decision apparatus performs data analysis on the first data type, the cloud server sends the data analysis indication of the first data type to the data decision apparatus in order to instruct the data decision apparatus to perform data analysis on the first data satisfying the first data type.

Moreover, after receiving the data analysis indication, the data decision apparatus determines a task that data analysis needs to be performed on the first data satisfying the first data type.

In step 305, when the data decision apparatus obtains the first data satisfying the first data type, because the data decision apparatus already receives the data analysis indication sent by the cloud server, the data decision apparatus performs data analysis on the first data to obtain the analysis result for the first data.

Description is performed by still using an example in step 301 to step 304. When the data decision apparatus obtains the blood pressure value generated by the blood pressure monitor, the data decision apparatus performs data analysis on the first data, that is, compare the blood pressure value with the healthy blood pressure range. For example, after the blood pressure value is compared with the healthy blood pressure range, the analysis result for the first data is: a current blood pressure value of the user is greater than a normal blood pressure range.

For a method for the data decision apparatus to perform data analysis on the first data to obtain the analysis result for the first data, reference may be made to step 104, and details are not described herein again.

In step 306, corresponding to step 305, when the data decision apparatus obtains the second data, where the second data is data that does not satisfy the first data type, because the data decision apparatus has not received a data analysis indication, for the second data, sent by the cloud server, the data decision apparatus sends the second data to the cloud server.

In step 307, after obtaining the second data sent by the data decision apparatus, the cloud server performs data analysis on the second data to obtain the analysis result for the second data.

For a method for the cloud server to perform data analysis on the second data and obtain the analysis result for the second data, reference may be made to the method for the data decision apparatus to perform data analysis on the first data and obtain the analysis result for the first data.

Certainly, information about the user and historical information of a user operation are stored in the cloud server, and therefore, when performing data analysis on the second data, the cloud server may invoke the information about the user and the historical information of the user operation, and generate a more all-around analysis result. For example, when the second data is current location information of the user, the cloud server may provide a more all-around analysis result to the user according to already stored historical information of the user at a current location.

In step 308, after obtaining the analysis result for the first data, the data decision apparatus may generate the first decision data according to the analysis result for the first data, where the first decision data is decision information of a data characteristic reflected for the first data.

Further, for a method for the data decision apparatus to perform data analysis and data decision on the first data in order to generate the first decision data, reference may be made to step 104, and details are not described herein again.

In step 309, after generating the first decision data, the data decision apparatus may send the first decision data to the cloud server such that the cloud server modifies the first decision data and obtain more accurate decision data.

Additionally, at the same time of sending the first decision data to the cloud server, the data decision apparatus may further send the first decision data to each human body device or display the first decision data on a display interface of the data decision apparatus. In this way, the user may obtain, at first time, decision information about perception data generated by multiple human body devices possessed by the user, thereby improving analysis efficiency for the perception data.

In step 310, the cloud server modifies, according to the analysis result for the second data, the first decision data sent by the data decision apparatus, and obtains the second decision data after the modification.

After the data decision apparatus obtains the analysis result for the first data, the data decision apparatus may perform data decision on the analysis result for the first data, and obtain the first decision data. However, in the first decision data obtained by the data decision apparatus, only some perception data determined by the storage space information and the computing rate information of the data decision apparatus and the information about the communication rate between the data decision apparatus and the cloud server is considered. When multiple pieces of perception data obtained by the data decision apparatus include second data, where a data analysis task of the second data type does not satisfy the analysis conditions in step 201, the data decision apparatus cannot perform data analysis on the second data, and therefore, the first decision data obtained by the data decision apparatus is not all-around.

Therefore, a data decision model library may also be stored in the cloud server in advance. Similar to the data analysis model library, the data decision model library may include data decision models for multiple analysis results and for details, reference may be made to step 104, and the cloud server may modify the first decision data according to a data decision model.

For example, first decision information that the data decision apparatus reports to the cloud server is: the user tumbles, and needs a medicine for treating bruise, and an analysis result of the cloud server for the second data is: there are two drugstores within one kilometer away from a current location of the user, and then, the cloud server may modify the first decision information according to a related data decision model in the data decision model library, and provide a roadmap of a nearer drugstore to the user.

In step 311, the cloud server sends the second decision data to the data decision apparatus such that the data decision apparatus feeds back the second decision data to the user.

It can be seen that, by modifying the first decision information generated by the data decision apparatus, the cloud server may provide more all-around data decision information to the user, thereby resolving, to an extent, a problem in the prior art that multiple human body devices cannot effectively coordinate to separately perceive the perception data, and improving analysis quality for the perception data.

Figure 4:
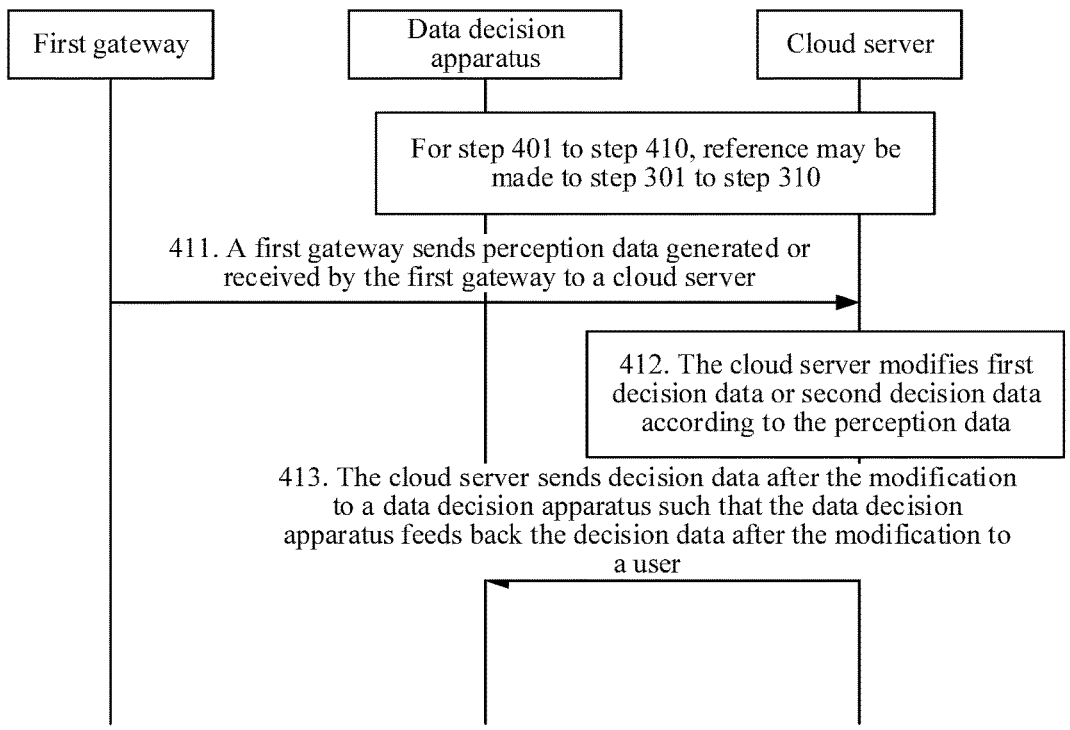
FIG. 4 is a schematic interaction diagram of a data decision method according to an embodiment of the present disclosure.

An embodiment of the present disclosure provides a data decision method. As shown in FIG. 4, for step 401 to step 410, reference may be made to step 301 to step 310, and after step 410, the method further includes step 411 to step 413.

Step 411: A first gateway sends perception data generated or received by the first gateway to a cloud server.

Step 412: The cloud server modifies first decision data or second decision data according to the perception data.

Step 413: The cloud server sends decision data after the modification to a data decision apparatus such that the data decision apparatus feeds back the decision data after the modification to a user.

The cloud server may further perform data exchange with the first gateway, where the first gateway is any gateway except the data decision apparatus, such as a home gateway installed in a home, or an automobile gateway installed in an automobile. Perception data generated by a human body device can reflect, only to an extent, current various indexes of a human body, and therefore, the first decision data or the second decision data cannot provide most accurate decision information to the user all around. In this way, the cloud server may further modify, according to the perception data generated or received by the first gateway, the first decision data generated by the data decision apparatus, or the second decision data generated by the cloud server, thereby improving analysis quality for the perception data.

In step 411, the cloud server may first obtain the perception data reported by the first gateway, such as a temperature value reported by the home gateway, or video surveillance data. It should be noted that, the cloud server may obtain, at any moment of performing step 401 to step 410, the perception data reported by the first gateway, that is, there is no temporal logic relationship between step 411 and step 401 to step 410.

In step 412, after obtaining the perception data reported by the first gateway, the cloud server may modify, according to the perception data, the first decision data obtained by the cloud server in step 409, or, the cloud server may modify, according to the perception data, the second decision data generated by the cloud server in step 410.

For example, the first decision data sent by the data decision apparatus is: weight of the user is excessive, and the user is advised to strengthen exercise, and video data reported by the home gateway indicates that the user takes in excessive calories in a month. Then, the cloud server may modify the first decision data according to the video data, for example, advise the user to reduce calorie intake at the same time of strengthening exercise. It can be seen that, the data decision apparatus can obtain only the perception data generated by the human body device, and the perception data can reflect only various human body indexes of the user, and therefore, the first decision data that is sent by the data decision apparatus and that is obtained by the cloud server may be not all-around, and the perception data reported by the first gateway may help the cloud server obtain more all-around decision data about the user.

Certainly, similar to the data decision apparatus, the first gateway may also perform initial analysis and decision on the obtained perception data, generate fourth decision data, and then send the fourth decision data generated by the first gateway to the cloud server. In this way, the cloud server may further modify the first decision data or the second decision data according to the fourth decision data without a need of obtaining all perception data of the first gateway, and a speed at which further modification is performed on the first decision data or the second decision data may be improved at the same time of alleviating a computing burden on the cloud server.

Finally, in step 413, the cloud server sends the decision data after the modification in step 412 to the data decision apparatus such that the data decision apparatus feeds back the decision data after the modification to the user.

It can be seen that, when further modification is performed on the first decision data or the second decision data, because the cloud server performs more all-around comprehensive deep analysis on the first decision data or the second decision data with reference to the perception data reported by the first gateway, it can be ensured that the decision data after the modification in step 412 is more accurate, thereby improving analysis quality for the perception data.

This embodiment of the present disclosure provides a data decision method, where a data decision apparatus obtains analysis conditions for data analysis, and then reports the analysis conditions to a cloud server in order to determine a first data type that can be processed, where when the data decision apparatus obtains first data satisfying the first data type, the first data is perception data generated by a human body device connected to the data decision apparatus, and performs data analysis and data decision on the first data, and generates first decision data, where the first decision data is decision information of a data characteristic reflected for the first data. It can be seen that, the data decision apparatus may perform rapid and relatively accurate data analysis and decision on various perception data satisfying the first data type, and then may feedback the obtained first decision data to the human body device and a user at first time, thereby resolving, to an extent, a problem that multiple human body devices cannot effectively coordinate to separately perceive the perception data, and improving analysis quality for the perception data.

Figure 5:
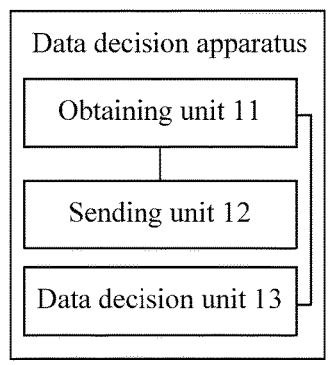
FIG. 5 is a schematic structural diagram of a data decision apparatus according to an embodiment of the present disclosure.

FIG. 5 is a schematic structural diagram of a data decision apparatus according to an embodiment of the present disclosure. The data decision apparatus provided in this embodiment of the present disclosure may be configured to implement the methods implemented in the embodiments of the present disclosure shown in FIG. 1 to FIG. 4. For convenience of description, only a part related to the embodiments of the present disclosure is shown, and for specific technical details that are not disclosed, refer to the embodiments of the present disclosure shown in FIG. 1 to FIG. 4.

Exemplarily, the data decision apparatus further includes an obtaining unit 11 configured to obtain analysis conditions for data analysis, where the analysis conditions refer to storage space information and computing rate information of the data decision apparatus and information about a communication rate between the data decision apparatus and a cloud server, where the cloud server is connected to the data decision apparatus, and obtain first data satisfying the first data type, where the first data is perception data generated by a human body device connected to the data decision apparatus, a sending unit 12 configured to report the analysis conditions in the obtaining unit 11 to the cloud server such that the cloud server determines, according to the analysis conditions, the first data type that the data decision apparatus can process, and a data decision unit 13 configured to perform data analysis and data decision on the first data in the obtaining unit 11, and generate first decision data, where the first decision data is decision information of a data characteristic reflected for the first data.

Figure 6:
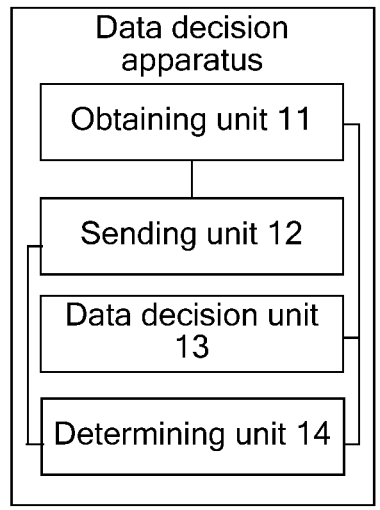
FIG. 6 is a schematic structural diagram of a data decision apparatus according to an embodiment of the present disclosure.

As shown in FIG. 6, the data decision apparatus further includes a determining unit 14, where the determining unit 14 is configured to determine a second data type according to the analysis conditions in the obtaining unit 11. The sending unit 12 is further configured to send the second data type in the determining unit 14 to the cloud server such that the cloud server determines, according to the analysis conditions, whether the data decision apparatus has a capability to process the second data type, and the obtaining unit 11 is further configured to obtain first data satisfying the first data type or the second data type when a message that the cloud server allows the data decision apparatus to process data of the second data type is received.

The determining unit 14 is further configured to determine whether the first data type is consistent with the second data type, and the sending unit 12 is further configured to send the second data type to the cloud server when the first data type is inconsistent with the second data type in the determining unit 14 such that the cloud server determines, according to the analysis conditions, whether the data decision apparatus has the capability to process the second data type.

The sending unit 12 is further configured to send the second data to the cloud server when second data that does not satisfy the first data type is received such that the cloud server performs data analysis according to the second data in order to obtain an analysis result for the second data.

The sending unit 12 is further configured to send the first decision data to the cloud server such that the cloud server modifies the first decision data according to the analysis result for the second data, and obtains second decision data after the modification, where the second decision data is decision information of a data characteristic reflected for the second data and the first decision data.

The sending unit 12 is further configured to send the first data and the first decision data to the cloud server such that the cloud server modifies the first decision data according to the first data and the second data, and obtains third decision data after the modification, where the third decision data is decision information of a data characteristic reflected for the first data and the second data.

Additionally, it should be noted that, the data decision apparatus provided in this embodiment of the present disclosure may be an MPS, where the MPS is a logic device unit configured to assist a person in performing communication, management, and data analysis on a human body device belonging to the person.

Further, the MPS may automatically determine a manner of communication between human body devices such as an implantable device, a wearable device, and a portable device (such as BLUETOOTH, WI-FI, or ZIGBEE (ZIGBEE protocol, which is a low power consumption local area network protocol based on the Institute of Electrical and Electronics Engineers (IEEE) standard an IEEE802.15.4 standard), to perform individual networking or hybrid networking), maintain and optimize network running, and serve as a communications gateway from a human body device to the Internet. The MPS may be further responsible for performing, to an extent, data analysis on perception data, such as a heart rate and a blood pressure of a human body, a temperature and water, electricity and gas usage situations of a home environment, and an automobile running state collected from the human body and an environment, such as a home or an automobile, and performing data exchange with the cloud server, and the MPS may be integrated into a smart device or exist as a physical device, which is not limited in the present disclosure.

Figure 7:
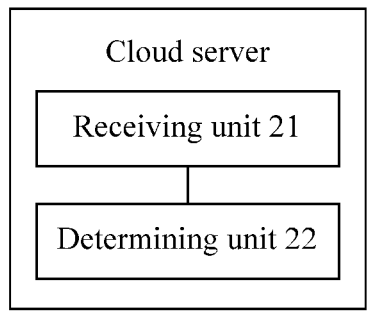
FIG. 7 is a schematic structural diagram of a cloud server according to an embodiment of the present disclosure.

FIG. 7 is a schematic structural diagram of a cloud server according to an embodiment of the present disclosure. The server provided in this embodiment of the present disclosure may be configured to implement the methods implemented in the embodiments of the present disclosure shown in FIG. 1 to FIG. 4. For convenience of description, only a part related to the embodiments of the present disclosure is shown, and for specific technical details that are not disclosed, refer to the embodiments of the present disclosure shown in FIG. 1 to FIG. 4.

Exemplarily, the server includes a receiving unit 21 configured to receive analysis conditions for data analysis that are sent by a data decision apparatus, where the analysis conditions refer to storage space information and computing rate information of the data decision apparatus and information about a communication rate between the data decision apparatus and the cloud server, where the cloud server is connected to the data decision apparatus, and a determining unit 22 configured to determine, according to the analysis conditions in the receiving unit 21, a first data type that the data decision apparatus can process such that the data decision apparatus performs data analysis and data decision on first data satisfying the first data type, and generates first decision data.

Figure 8:
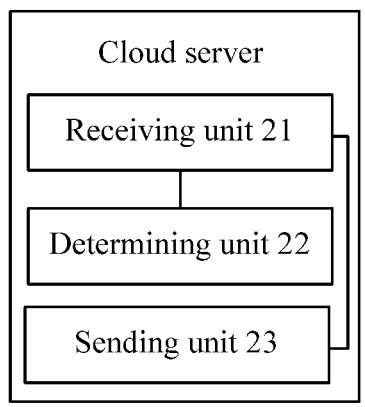
FIG. 8 is a schematic structural diagram of a cloud server according to an embodiment of the present disclosure.

As shown in FIG. 8, the cloud server further includes a sending unit 23, where the receiving unit 21 is further configured to receive a second data type sent by the data decision apparatus, where the second data type is determined by the data decision apparatus according to the analysis conditions, and the sending unit 23 is configured to send, to the data decision apparatus, a message for allowing the data decision apparatus to process data of the second data type if the cloud server determines according to the analysis conditions that the data decision apparatus has a capability to process the second data type such that the data decision apparatus obtains first data satisfying the first data type or the second data type.

The determining unit 22 is further configured to determine, according to the analysis conditions, whether to allow to perform data analysis on the first data, and send a data analysis indication for the first data to the data decision apparatus in order to instruct the data decision apparatus to perform data analysis on the first data if it is allowed to perform data analysis on the first data.

Figure 9:
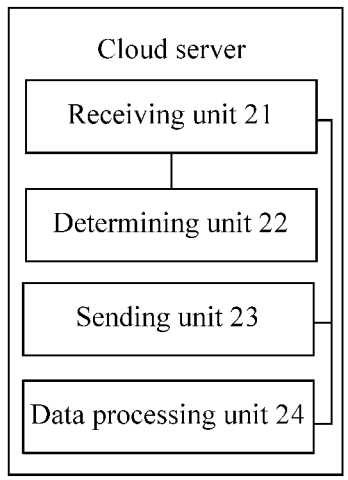
FIG. 9 is a schematic structural diagram of a cloud server according to an embodiment of the present disclosure.

As shown in FIG. 9, the cloud server further includes a data processing unit 24, where the receiving unit 21 is further configured to receive second data and the first decision data sent by the data decision apparatus, where the second data refers to perception data that does not satisfy the first data type, and the data processing unit 24 is configured to perform data analysis according to the second data in the receiving unit 21 in order to obtain an analysis result for the second data, and modify the first decision data according to the analysis result for the second data, and obtain first decision data after the modification.

The receiving unit 21 is further configured to receive the first data sent by the data decision apparatus, and the data processing unit 24 is further configured to modify the first decision data according to the first data in the receiving unit 21 and the analysis result for the second data, and obtain first decision data after the modification.

The receiving unit 21 is further configured to obtain perception data sent by a first gateway, where the first gateway refers to any gateway except the data decision apparatus, and the data processing unit 24 is further configured to modify the first decision data according to the perception data obtained by the first gateway in the receiving unit 21.

It should be noted that, the cloud server provided in this embodiment of the present disclosure may be one or multiple in quantity, for example, a cloud platform of multiple cloud server components. Information about and historical data of each user may be stored in the cloud platform, and the cloud platform may perform deep and precise calculation by invoking the information about and the historical data of each user when performing cloud computing.

Further, the cloud platform may be configured to store perception data generated by each human body device, and perform data analysis on the perception data collected from each human body device, and extract a change characteristic and law of the data. For example, the cloud platform may calculate a change law of human body blood pressures in one year, a content change law of human body alcohol in one year, and the like. Additionally, the cloud platform may further perform association analysis according to a data analysis result, provide decision and advice information. For example, if finding that increase in a blood pressure is caused by drinking, the cloud platform sends alarm information and an action advice to a master using an MPS, for example, stopping drinking, or limiting a drinking amount to a value. Certainly, the cloud platform may further communicate with the MPS, that is, configure and manage a parameter of the MPS. For example, an adult may log in to the cloud platform to remotely configure and manage an MPS of a kid, which is not limited in the present disclosure.

This embodiment of the present disclosure provides a data decision apparatus, where the data decision apparatus obtains analysis conditions for data analysis, and then reports the analysis conditions to a cloud server in order to determine a first data type that can be processed, where when the data decision apparatus obtains first data satisfying the first data type, the first data is perception data generated by a human body device connected to the data decision apparatus, and performs data analysis and data decision on the first data, and generates first decision data, where the first decision data is decision information of a data characteristic reflected for the first data. It can be seen that, the data decision apparatus may perform rapid and relatively accurate data analysis and decision on various perception data satisfying the first data type, and then may feedback the obtained first decision data to the human body device and a user at first time, thereby resolving, to an extent, a problem that multiple human body devices cannot effectively coordinate to separately perceive the perception data, and improving analysis quality for the perception data.

Figure 10:
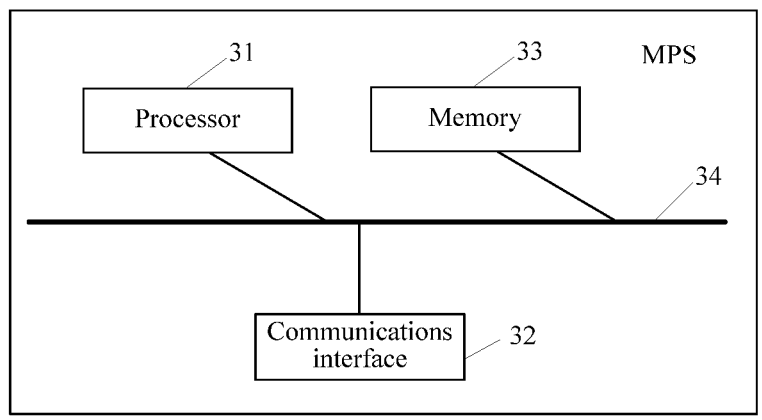
FIG. 10 is a schematic hardware diagram of a mobile personal station (MPS) according to an embodiment of the present disclosure.

FIG. 10 is a schematic hardware diagram of an MPS according to an embodiment of the present disclosure, where the MPS is a logic device unit configured to assist a person in performing communication, management, and data analysis on a device belonging to the person or a related device, and the MPS may be the data decision apparatus in the foregoing embodiment. The MPS provided in this embodiment of the present disclosure may be configured to implement the methods implemented in the embodiments of the present disclosure shown in FIG. 1 to FIG. 4. For convenience of description, only a part related to the embodiments of the present disclosure is shown, and for specific technical details that are not disclosed, refer to the embodiments of the present disclosure shown in FIG. 1 to FIG. 4.

As shown in FIG. 10, the MPS includes a processor 31, a communications interface 32, a memory 33 and a bus 34.

The processor 31, the communications interface 32 and the memory 33 communicate with each other using the bus 34.

The processor 31 is a control center of the MPS, and the processor 31 executes various functions of the MPS and processes data by running or executing a software program and/or module stored in the memory 33, and invoking data stored in the memory 33.

The communications interface 32 may be implemented by an optical communications interface, an electrical communications interface, a wireless communications interface or any combination thereof. For example, the optical communications interface may be a small form-factor pluggable (SFP) communications interface, an enhanced SFP (SFP+) communications interface or a 10 Gigabit SFP (XFP) communications interface. The electrical communications interface may be an Ethernet network interface controller (NIC). The wireless communications interface may be a wireless NIC (WNIC). There may be multiple communications interfaces 32 at a receive end.

The memory 33 may be configured to store a software program or data, and the processor 31 executes various function applications and data processing of the MPS by running the software program or data stored in the memory 33.

In this embodiment of the present disclosure, the communications interface 32 of the MPS obtains analysis conditions for data analysis and stores the analysis conditions in the memory 33, where the analysis conditions include storage space information and computing rate information of the MPS and information about a communication rate between the MPS and a cloud server. The processor 31 invokes the communications interface 32 to report the analysis conditions to the cloud server such that the cloud server determines, according to the analysis conditions, a first data type that the MPS can process. When obtaining first data satisfying the first data type, the communications interface 32 sends the first data to the processor 31, where the first data is perception data generated by a human body device connected to the MPS, and the processor 31 performs data analysis and data decision on the first data, generates first decision data, and stores the first decision data in the memory 33, where the first decision data is decision information of a data characteristic reflected for the first data.

After the communications interface 32 of the MPS obtains the analysis conditions for data analysis, the following step may be further included. The processor 31 determines second data type according to the analysis conditions obtained by the communications interface 32. The processor 31 invokes the communications interface 32 to send the second data type to the cloud server such that the cloud server determines, according to the analysis conditions, whether the MPS has a capability to process the second data type, and when receiving a message that the cloud server allows the MPS to process data of the second data type, the communications interface 32 sends the message to the processor 31. In this way, the processor 31 may obtain first data satisfying the first data type or the second data type.

The following step may be further included before the processor 31 invokes the communications interface 32 to send the second data type to the cloud server. The processor 31 determines whether the first data type is consistent with the second data type, and when the first data type is inconsistent with the second data type, the processor 31 invokes the communications interface 32 to send the second data type to the cloud server such that the cloud server determines, according to the analysis conditions, whether the MPS has the capability to process the second data type.

After the communications interface 32 of the MPS obtains the analysis conditions for data analysis and stores the analysis conditions in the memory 33, the following step may be further included. The communications interface 32 sends the second data to the cloud server when receiving second data that does not satisfy the first data type such that the cloud server performs data analysis according to the second data in order to obtain an analysis result for the second data.

After the processor 31 performs data analysis and data decision on the first data, and generates the first decision data, the following step may be further included. The processor 31 sends the first decision data to the cloud server using the communications interface 32 such that the cloud server modifies the first decision data according to the analysis result for the second data, and obtains second decision data after the modification, where the second decision data is decision information of a data characteristic reflected for the second data and the first decision data.

Alternatively, after the processor 31 performs data analysis and data decision on the first data, and generates the first decision data, the following step may be further included. The processor 31 sends the first data and the first decision data to the cloud server using the communications interface 32 such that the cloud server modifies the first decision data according to the first data and the second data, and obtains third decision data after the modification, where the third decision data is decision information of a data characteristic reflected for the first data and the second data.

Figure 11:
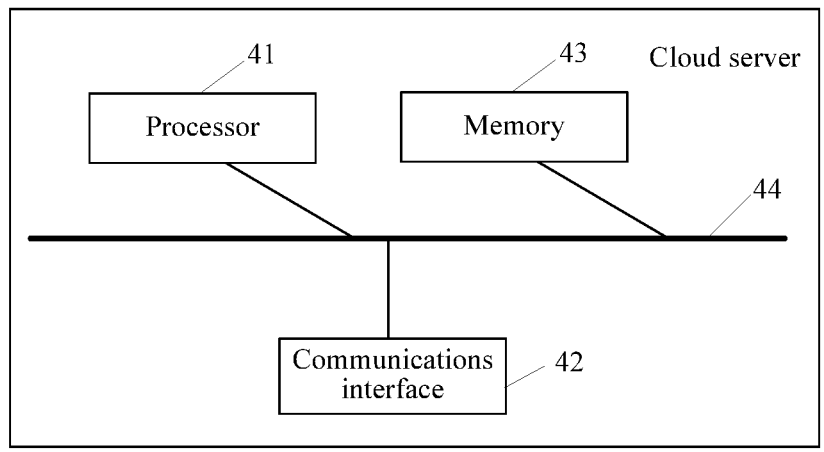
FIG. 11 is a schematic hardware diagram of a cloud server according to an embodiment of the present disclosure.

Correspondingly, FIG. 11 is a schematic hardware diagram of a cloud server according to the present disclosure.

The cloud server provided in this embodiment of the present disclosure may be one or multiple in quantity, for example, a cloud platform of multiple cloud server components. Information about and historical data of each user may be stored in the cloud platform, and when performing cloud computing, the cloud platform may perform deep and precise calculation by invoking the information about and the historical data of each user.

As shown in FIG. 11, the cloud server includes a processor 41, a communications interface 42, a memory 43 and a bus 44.

The processor 41, the communications interface 42 and the memory 43 communicate with each other using the bus 44.

The processor 41 is a control center of the cloud platform, and the processor 41 executes various functions of the cloud platform and processes data by running or executing a software program and/or module stored in the memory 43, and invoking data stored in the memory 43.

The communications interface 42 may be implemented by an optical communications interface, an electrical communications interface, a wireless communications interface or any combination thereof. For example, the optical communications interface may be an SFP communications interface, an SFP+ communications interface or an XFP communications interface. The electrical communications interface may be an Ethernet NIC. The wireless communications interface may be a WNIC. There may be multiple communications interfaces 42 at a receive end.

The memory 43 may be configured to store a software program or data, and the processor 41 executes various function applications and data processing of the cloud platform by running the software program or data stored in the memory 43.

In this embodiment of the present disclosure, the processor 41 of the cloud server receives, using the communications interface 42, analysis conditions for data analysis sent by an MPS, and stores the analysis conditions in the memory 43, where the analysis conditions include storage space information and computing rate information of the MPS and information about a communication rate between the MPS and the cloud server. The processor 41 determines, according to the analysis conditions, a first data type that the MPS can process such that the MPS performs data analysis and data decision on first data satisfying the first data type, and generates first decision data.

After the processor 41 of the cloud server receives, using the communications interface 42, the analysis conditions for data analysis that are sent by the MPS, the following step may be further included. The communications interface 42 receives second data type sent by the MPS and sends the second data type to the processor 41, where the second data type is determined by the MPS according to the analysis conditions, and the processor 41 determines, according to the analysis conditions, whether the MPS has a capability to process the second data type, and if the cloud server determines according to the analysis conditions that the MPS has a capability to process the second data type, the processor 41 invokes the communications interface 42 to send, to the MPS, a message for allowing the MPS to process data of the second data type such that the MPS obtains first data satisfying the first data type or the second data type.

After the processor 41 of the cloud server receives, using the communications interface 42, the analysis conditions for data analysis sent by the MPS, the following step may be further included. The communications interface 42 receives second data sent by the MPS and the first decision data and sends the second data and the first decision data to the processor 41, where the second data refers to perception data that does not satisfy the first data type. The processor 41 performs data analysis according to the second data in order to obtain an analysis result for the second data, and the processor 41 modifies the first decision data according to the analysis result for the second data, and obtains first decision data after the modification.

The processor 41 of the cloud server may further receive, using the communications interface 42, the first data sent by the MPS. In this case, the processor 41 modifies the first decision data according to the first data and the analysis result for the second data, and obtains the first decision data after the modification.

The processor 41 of the cloud server may further receive, using the communications interface 42, perception data sent by a first gateway and send the perception data to the processor 41, where the first gateway refers to any gateway except the MPS, and the processor 41 modifies the first decision data according to the perception data obtained by the first gateway.

This embodiment of the present disclosure provides a data decision apparatus, where the data decision apparatus obtains analysis conditions for data analysis, and then reports the analysis conditions to a cloud server in order to determine a first data type that can be processed, where when the data decision apparatus obtains first data satisfying the first data type, the first data is perception data generated by a human body device connected to the data decision apparatus, and performs data analysis and data decision on the first data, and generates first decision data, where the first decision data is decision information of a data characteristic reflected for the first data. It can be seen that, the data decision apparatus may perform rapid and relatively accurate data analysis and decision on various perception data satisfying the first data type, and then may feedback the obtained first decision data to the human body device and a user at first time, thereby resolving, to an extent, a problem that multiple human body devices cannot effectively coordinate to separately perceive the perception data, and improving analysis quality for the perception data.

Figure 12:
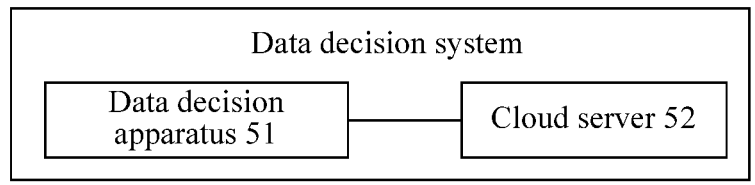
FIG. 12 is a schematic structural diagram of a data decision system according to an embodiment of the present disclosure.

FIG. 12 shows a data decision system provided in an embodiment of the present disclosure, including a data decision apparatus 51, and a cloud server 52 connected to the data decision apparatus 51.

For details of a method for interaction between the data decision apparatus 51 and the cloud server 52, reference may be made to Embodiment 1 to Embodiment 4, and therefore details are not described herein again.

Figure 13:
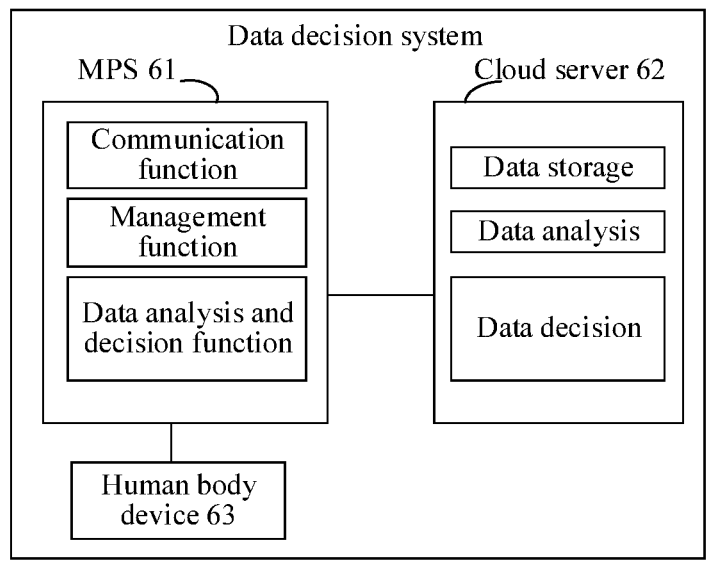
FIG. 13 is a schematic structural diagram of a data decision system according to an embodiment of the present disclosure.

Exemplarily, a data decision system shown in FIG. 13 includes an MPS 61 as a data decision apparatus. Further, the data decision system includes a cloud server 62 connected to the MPS 61, and each human body device 63 connected to the MPS 61.

The MPS 61 may be integrated into a smart device or exist as a physical device. Herein, the MPS 61 may be used as an individual physical device, and be loaded with a corresponding operating system and various applications to be used by a user.

Further, the MPS 61 may be integrated with functions such as communication, management, and data analysis and decision. For example, the MPS 61 may automatically determine a manner of communication between human body devices 63 such as an implantable device, a wearable device and a portable device (such as BLUETOOTH, WI-FI or ZIGBEE, to perform individual networking or hybrid networking) and maintain and optimize network running, or the MPS 61 may manage each human body device 63 connected to the MPS 61, various parameters of the human body device 63 are configured in the MPS 61, and the MPS 61 serves as a communications gateway from the human body device 63 to the Internet. The MPS 61 may be further responsible for performing, to an extent, data analysis on perception data (such as a heart rate and a blood pressure of a human body, a temperature and water, electricity and gas usage situations of a home environment, and an automobile running state) collected from the human body and an environment (such as a home or an automobile), and performing data exchange with the cloud server 62 in order to finally obtain decision data and feedback the decision data to each human body device 63 and the user.

Additionally, the cloud server 62 may also be integrated with functions such as data storage, data analysis, and data decision. For example, the cloud platform may be configured to store perception data generated by each human body device 63, and perform data analysis on the perception data collected from each human body device 63, and extract a change characteristic and law of the data. For example, the cloud platform may calculate a change law of human body blood pressures in one year, a content change law of human body alcohol in one year, and the like. Additionally, the cloud platform may further perform association analysis according to a data analysis result, provide decision and advice information. For example, if finding that increase in a blood pressure is caused by drinking, the cloud platform sends alarm information and an action advice to a master using the MPS 61, for example, stopping drinking, or limiting a drinking amount to a value.

Exemplarily, before the MPS 61 and the cloud server 62 perform data decision according to the received perception data of the human body device 63, the cloud server 62 needs to perform configuration on a data analysis capability of the MPS 61, that is, the cloud server 62 indicates, to the MPS 61, data that may be analyzed by the MPS 61, and data on which data analysis needs to be performed by the cloud server 62. In this way, when the MPS 61 obtains multiple pieces of perception data reported by multiple human body devices 63, the MPS 61 may rapidly perform analysis and decision on some data according to a result of the foregoing configuration, and provide a decision result to each human body device 63 and the user at first time. Certainly, at the same time, the cloud server 62 may further perform deep comprehensive analysis on the perception data, then modify the decision data obtained by the MPS 61, and provide a more precise decision result after the modification to each human body device 63 and the user.

Further, this embodiment of the present disclosure provides two methods for the cloud server 62 to perform configuration on the analysis conditions for the MPS 61 to perform data analysis.

In a method 1, the MPS 61 may actively report, according to the analysis conditions for the MPS 61 to perform data analysis (for example, storage space information and computing rate information of the MPS 61 and information about a communication rate between the MPS 61 and the cloud server 62), particular data that satisfies the foregoing analysis conditions and that is of the MPS 61 to the cloud server 62. For example, available storage space of the MPS 61 is 8 GB, a load value of the MPS 61 is 500 MHz (where idle resources of the MPS 61 account for 80%), and an available communication rate between the MPS 61 and the cloud server is 100 Mbps. Moreover, when a relationship between a blood pressure value reported by a blood pressure monitor and a blood pressure risk value is analyzed, only a load value of 50 MHz and storage space of 100 MB need to be consumed. Therefore, the MPS 61 may send a data analysis request to the cloud server 62, where the data analysis request requests the cloud server 62 to allow the MPS 61 to perform data analysis on the blood pressure value. Further, after the cloud server 62 sends a data analysis allowance response to the MPS 61 in order to allow the MPS 61 to perform data analysis on the blood pressure value, a process in which the cloud server 62 performs configuration on the data analysis capability of the MPS 61 is completed for once.

In a method 2, after the MPS 61 reports the analysis conditions for the MPS 61 to perform data analysis to the cloud server 62, the cloud server 62 determines, according to the analysis conditions, data that may be analyzed by the MPS 61, and data on which data analysis needs to be performed by the cloud server 62, and sends a data analysis indication to the MPS 61 such that the MPS 61 determines, according to the data analysis indication, data on which data analysis needs to be performed.

Further, after the cloud server 62 indicates, to the MPS 61, data that may be analyzed by the MPS 61, and data on which data analysis needs to be performed by the cloud server 62, for example, if gesture data perceived by a human body gesture detector and a heart rate value perceived by a heart rate monitor may be analyzed by the MPS 61, when the perception data reported by the multiple human body devices 63 and obtained by the MPS 61 includes the gesture information and the heart rate value, the MPS 61 separately performs analysis on the gesture information and the heart rate value. For example, an analysis result of the MPS 61 for the gesture information is that the human body is in a violent exercise state, and an analysis result of the MPS 61 for the heart rate value is that the heart rate accelerates. In this case, the MPS 61 performs decision according to these two obtained analysis results. For example, acceleration of the heart rate in the violent exercise state belongs to a normal phenomenon, and therefore, the MPS 61 may obtain first decision data that a current physiological index of the user is normal, and feedback the first decision data to the user at first time.

Further, to ensure accuracy of the first decision data generated by the MPS 61, the cloud server 62 may further modify the first decision data. Further, the MPS 61 sends the generated first decision data to the cloud server 62. Because storage space and a calculation capability of the cloud server 62 are both far greater than those of the MPS 61, and a large quantity of historical data of each user is stored in the cloud server 62, the cloud server 62 may further modify the first decision data. For example, the cloud server 62 obtains the first decision data that the current physiological index of the user is normal, and the cloud server 62 obtains, by querying user information of the user, historical information that the user is a cardiac patient. Then, the cloud server 62 modifies the first decision data according to the historical information, and then obtains second decision data after the modification. For example, the cloud server 62 generates the second decision data for advising the user to reduce an exercise strength, and sends the second decision data to the MPS 61 such that the MPS 61 feeds back the second decision data to the user. Certainly, the cloud server 62 may further obtain perception data of each human body device 63 from the MPS 61, and then perform analysis and decision on the obtained perception data without a need of performing analysis and decision according to the first decision data generated by the MPS 61, which is not limited in the present disclosure.

Figure 14:
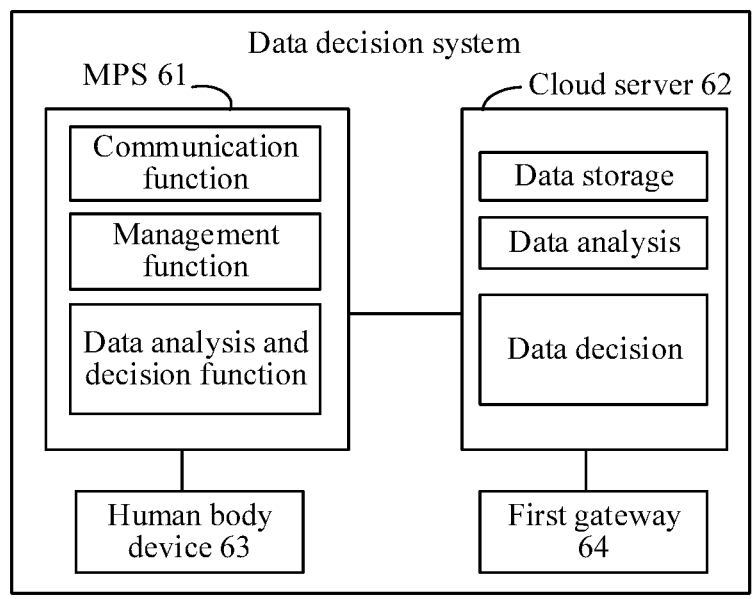
FIG. 14 is a schematic structural diagram of a data decision system according to an embodiment of the present disclosure.

Further, as shown in FIG. 14, with respect to the data decision system in FIG. 13, the data decision system may further include a first gateway 64, where the first gateway 64 and the MPS 61 are both connected to the cloud server 62, and the first gateway 64 is any gateway except the data decision apparatus, such as a home gateway installed in a home, or an automobile gateway installed in an automobile.

Further, the cloud server 62 may first obtain perception data reported by the first gateway 64 such as a home gateway. Then, when further modifying the first decision data sent by the MPS 61, the cloud server 62 may perform more all-around data analysis on the first decision data according to the perception data reported by the first gateway 64, and then modify the first decision data according to an analysis result. For example, the first decision data sent by the MPS 61 includes weight of the user is excessive, and the user is advised to strengthen exercise, and video data reported by the home gateway indicates that the user takes in excessive calories in a month. Then, the cloud server 62 may modify the first decision data according to the video data, for example, advise the user to reduce calorie intake at the same time of strengthening exercise.

It can be seen that, when further modification is performed on the first decision data sent by the MPS 61, because the cloud server 62 performs comprehensive deep analysis on the first decision data with reference to the perception data reported by the first gateway 64, it can be ensured that modification performed by the cloud server 62 on the first decision data is more accurate, thereby improving analysis quality for the perception data.

Certainly, similar to the MPS 61, the first gateway 64 may also perform initial analysis and decision on the obtained perception data, and then send a decision result of the first gateway 64 to the cloud server 62. In this way, the cloud server 62 may further modify the first decision data according to the decision result of the first gateway 64 without a need of obtaining all perception data of the first gateway 64, and a speed at which the first decision data is further modified may be improved at the same time of alleviating a computing burden on the cloud server 62.

This embodiment of the present disclosure provides a data decision system, where a data decision apparatus, such as the MPS 61, in the system obtains analysis conditions for data analysis, and then reports the analysis conditions to a cloud server, such as the cloud server 62 in order to determine a first data type that can be processed, where when the data decision apparatus obtains first data satisfying the first data type, the first data is perception data generated by a human body device connected to the data decision apparatus, and performs data analysis and data decision on the first data, and generates first decision data, where the first decision data is decision information of a data characteristic reflected for the first data. It can be seen that, the data decision apparatus may perform rapid and relatively accurate data analysis and decision on various perception data satisfying the first data type, and then may feedback the obtained first decision data to the human body device and a user at first time, thereby resolving, to an extent, a problem that multiple human body devices cannot effectively coordinate to separately perceive the perception data, and improving analysis quality for the perception data.

It may be clearly understood by a person skilled in the art that, for the purpose of convenient and brief description, division of the foregoing functional modules is taken as an example for illustration. In actual application, the foregoing functions can be allocated to different functional modules and implemented according to a requirement, that is, an inner structure of an apparatus is divided into different functional modules to implement all or some of the functions described above. For a detailed working process of the foregoing system, apparatus, and unit, reference may be made to a corresponding process in the foregoing method embodiments, and details are not described herein again.

In the several embodiments provided in the present application, it should be understood that the disclosed system, apparatus, and method may be implemented in other manners. For example, the described apparatus embodiment is merely exemplary. For example, the module or unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected according to actual needs to achieve the objectives of the solutions of the embodiments.

In addition, functional units in the embodiments of the present disclosure may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of the present disclosure essentially, the part, or all or some of the technical solutions may be implemented in the form of a software product. The computer software product is stored in a storage medium and includes several instructions for instructing a computer device, which may be a personal computer, a server, or a network device or a processor to perform all or some of the steps of the methods described in the embodiments of the present disclosure. The foregoing storage medium includes any medium that can store program code, such as a universal serial bus (USB) flash drive, a removable hard disk, a read-only memory (ROM), a random access memory (RAM), a magnetic disk, or an optical disc.

The foregoing descriptions are merely specific implementation manners of the present disclosure, but are not intended to limit the protection scope of the present disclosure. Any variation or replacement readily figured out by a person skilled in the art within the technical scope disclosed in the present disclosure shall fall within the protection scope of the present disclosure. Therefore, the protection scope of the present disclosure shall be subject to the protection scope of the claims.

What is claimed is:

1. A data decision method, comprising:
    obtaining, by a data decision apparatus, analysis conditions for data analysis, wherein the analysis conditions refer to storage space information and computing rate information of the data decision apparatus and information about a communication rate between the data decision apparatus and a cloud server, and wherein the cloud server is connected to the data decision apparatus;
    reporting, by the data decision apparatus, the analysis conditions to the cloud server;
    receiving, from the cloud server, a message indicating that the data decision apparatus has a capability to process a first data type;
    obtaining, by the data decision apparatus from a human body device coupled to the data decision apparatus, first data satisfying the first data type, wherein the first data is perception data and includes data regarding at least one human body characteristic of a user of the data decision apparatus;
    performing, by the data decision apparatus, data analysis on the first data to generate at least one analysis result regarding the at least one human body characteristic;
    performing, by the data decision apparatus, data decision on the at least one analysis result to determine an action regarding the user's health; and
    generating, by the data decision apparatus, first decision data based on the data decision, wherein the first decision data advises the user to take the action regarding the user's health.

2. The method of claim 1, wherein after reporting the analysis conditions to the cloud server, the method further comprises:
    determining, by the data decision apparatus, a second data type according to the analysis conditions;
    sending, by the data decision apparatus, the second data type to the cloud server; and
    obtaining, by the data decision apparatus, data satisfying the first data type or the second data type when the data decision apparatus receives a message indicating that the data decision apparatus comprises the capability to process data of the second data type.

3. The method of claim 2, wherein before sending the second data type to the cloud server, the method further comprises:
    determining, by the data decision apparatus, whether the first data type is consistent with the second data type; and
    sending, by the data decision apparatus, the second data type to the cloud server when the first data type is inconsistent with the second data type.

4. The method of claim 1, further comprising sending, by the data decision apparatus to the cloud server, second data that does not satisfy the first data type when the second data is received.

5. The method of claim 4, wherein after generating the first decision data, the method further comprises sending, by the data decision apparatus, the first decision data to the cloud server.

6. The method according to claim 4, wherein after generating the first decision data, the method further comprises sending, by the data decision apparatus, the first data and the first decision data to the cloud server.

7. A data decision method, comprising:
    receiving, by a cloud server, analysis conditions for data analysis from a data decision apparatus, wherein the analysis conditions refer to storage space information and computing rate information of the data decision apparatus and information about a communication rate between the data decision apparatus and the cloud server, and wherein the cloud server is connected to the data decision apparatus;
    determining, by the cloud server according to the analysis conditions, a first data type that the data decision apparatus can process;
    sending, by the cloud server to the data decision apparatus, an indication of the first data type;
    receiving, by the cloud server from the data decision apparatus, second data and first decision data, wherein the second data refers to data regarding at least one human body characteristic of a user of the data decision apparatus that does not satisfy the first data type, and wherein the first decision data advises the user of the data decision apparatus to take a first action regarding the user's health;

performing, by the cloud server, data analysis according to the second data in order to obtain an analysis result for the second data;

modifying, by the cloud server, the first decision data according to the analysis result for the second data to determine a second action regarding the user's health; and obtaining, by the cloud server, second decision data after the modification, wherein the second decision data advises the user to take the second action regarding the user's health.

8. The method according to claim 7, wherein after receiving the analysis conditions for the data analysis, the method further comprises:

receiving, by the cloud server, a second data type from the data decision apparatus; and sending, to the data decision apparatus, a message indicating that the data decision apparatus has a capability to process data of the second data type when the cloud server determines according to the analysis conditions that the data decision apparatus comprises the capability to process the second data type.

9. The method according to claim 1, wherein the first data is perception data received by the data decision apparatus from multiple human body devices connected to the data decision apparatus, wherein the at least one human body characteristic of the user comprises multiple human body characteristics respectively corresponding to the multiple human body devices, wherein the at least one analysis result comprises multiple analysis results respectively corresponding to the multiple human body characteristics, and wherein the data decision is further performed using the multiple analysis results and based on an association relationship between the multiple human body characteristics.

10. The method according to claim 7, wherein the cloud server further receives first data satisfying the first data type from the data decision apparatus, and wherein modifying the first decision data comprises modifying, by the cloud server, the first decision data according to the first data and the analysis result for the second data, and wherein obtaining the second decision data comprises obtaining, by the cloud server, the second decision data after modifying the first decision data.

11. The method according to claim 7, further comprising:

obtaining, by the cloud server, perception data from a first gateway, wherein the first gateway refers to any gateway except the data decision apparatus; and modifying, by the cloud server, the first decision data according to the perception data obtained from the first gateway.

12. A data decision apparatus, comprising:

a memory comprising instructions; and a processor coupled to the memory, wherein the instructions cause the processor to be configured to:

obtain analysis conditions for data analysis, wherein the analysis conditions refer to storage space information and computing rate information of the data decision apparatus and information about a communication rate between the data decision apparatus and a cloud server, and wherein the cloud server is connected to the data decision apparatus;

obtain, from a human body device coupled to the data decision apparatus, first data satisfying a first data type, wherein the first data is perception data and includes data regarding at least one human body characteristic of a user of the data decision apparatus;

report the analysis conditions to the cloud server;

receive, from the cloud server, a message indicating that the data decision apparatus has a capability to process the first data type;

perform data analysis on the first data to generate at least one analysis result regarding the at least one human body characteristic;

perform data decision on the at least one analysis result to determine an action regarding the user's health; and generate first decision data based on the data decision, wherein the first decision data advises the user to take the action regarding the user's health.

13. The data decision apparatus according to claim 12, wherein the instructions further cause the processor to be configured to:

determine a second data type according to the analysis conditions;

send the second data type to the cloud server to determine whether the data decision apparatus comprises a capability to process data of the second data type; and obtain data satisfying the first data type or the second data type when the data decision apparatus receives a message from the cloud server that indicates that the data decision apparatus has the capability to process data of the second data type.

14. The data decision apparatus according to claim 13, wherein the instructions further cause the processor to be configured to:

determine whether the first data type is consistent with the second data type; and send the second data type to the cloud server when the first data type is inconsistent with the second data type to cause the cloud server to determine, according to the analysis conditions, whether the data decision apparatus comprises the capability to process the second data type.

15. The data decision apparatus according to claim 12, wherein the instructions further cause the processor to be configured to send second data that does not satisfy the first data type to the cloud server when the second data that does not satisfy the first data type is received.

16. The data decision apparatus according to claim 15, wherein the instructions further cause the processor to be configured to send the first decision data to the cloud server.

17. The data decision apparatus according to claim 15, wherein the instructions further cause the processor to be configured to send the first data and the first decision data to the cloud server.

18. A cloud server, comprising:

a memory comprising instructions; and a processor coupled to the memory, wherein the instructions cause the processor to be configured to:

receive analysis conditions for data analysis from a data decision apparatus, wherein the analysis conditions refer to storage space information and computing rate information of the data decision apparatus and information about a communication rate between the data decision apparatus and the cloud server, and wherein the cloud server is connected to the data decision apparatus;

determine, according to the analysis conditions, a first data type that the data decision apparatus can process;

send, to the data decision apparatus, an indication of the first data type;

receive, from the data decision apparatus, second data and first decision data, wherein the second data refers to data regarding at least one human body characteristic of a user of the data decision apparatus that does not satisfy the first data type, and wherein the first decision data advises the user of the data decision apparatus to take a first action regarding the user's health;

perform data analysis according to the second data in order to obtain an analysis result for the second data;

modify the first decision data according to the analysis result for the second data to determine a second action regarding the user's health; and obtain second decision data after the modification, wherein the second decision data advises the user to take the second action regarding the user's health.

19. The cloud server according to claim 18, wherein the instructions further cause the processor to be configured to:
receive a second data type from the data decision apparatus; and
send, to the data decision apparatus, a message indicating that the data decision apparatus has a capability to process data of the second data type when the cloud server determines according to the analysis conditions that the data decision apparatus comprises the capability to process the second data type.

20. The cloud server according to claim 18, wherein the instructions further cause the processor to be configured to receive, from the data decision apparatus, first data satisfying the first data type, wherein the instructions that cause the processor to be configured to modify the first decision data further cause the processor to modify the first decision data according to the first data and the analysis result for the second data.

21. The cloud server according to claim 18, wherein the instructions further cause the processor to be configured to:
obtain perception data from a first gateway, wherein the first gateway refers to any gateway except the data decision apparatus; and
further modify the first decision data according to the perception data from the first gateway.

22. A data decision system, comprising:
a data decision apparatus; and
a cloud server connected to the data decision apparatus,
wherein the data decision apparatus comprises:
a first memory comprising first instructions; and
a first processor coupled to the first memory, wherein the fit instructions cause the first processor to be configured to:
obtain analysis conditions for data analysis, wherein the analysis conditions refer to storage space information and computing rate information of the data decision apparatus and information about a communication rate between the data decision apparatus and the cloud server;

obtain, from a human body device coupled to the data decision apparatus, first data satisfying a first data type, wherein the first data is perception data and includes data regarding at least one human body characteristic of a user of the data decision apparatus;

report the analysis conditions to the cloud server;

receive, from the cloud server, a message indicating that the data decision apparatus has a capability to process the first data type;

perform data analysis on the first data to generate at least one analysis result regarding the at least one human body characteristic;

perform data decision on the at least one analysis result to determine an action regarding the user's health; and generate first decision data based on the data decision, wherein the first decision data advises the user to take the action regarding the user's health, and wherein the cloud server, comprises:
a second memory comprising second instructions; and
a second processor coupled to the second memory, wherein the second instructions cause the second processor to be configured to:
receive the analysis conditions for the data analysis sent by the data decision apparatus; and
determine, according to the analysis conditions, the first data type that the data decision apparatus can process;
send, by the cloud server to the data decision apparatus, an indication of the first data type;
receive, by the cloud server from the data decision apparatus, second data and first decision data, wherein the second data refers to data regarding at least one human body characteristic of a user of the data decision apparatus that does not satisfy the first data type, wherein the first decision data advises the user of the data decision apparatus to take a first action regarding the user's health;
perform, by the cloud server, data analysis according to the second data in order to obtain an analysis result for the second data;
modify, by the cloud server, the first decision data according to the analysis result for the second data to determine a second action regarding the user's health; and
obtain, by the cloud server, second decision data after the modification, wherein the second decision data advises the user to take the second action regarding the user's health.

* * * * *

UNITED STATES PATENT AND TRADEMARK OFFICE
CERTIFICATE OF CORRECTION

PATENT NO.         : 10,484,248 B2
APPLICATION NO.    : 15/596862
DATED              : November 19, 2019
INVENTOR(S)        : Xijun Xue Page 1 of 1

It is certified that error appears in the above-identified patent and that said Letters Patent is hereby corrected as shown below:

In the Claims

Claim 22, Column 35, Line 50: "the fit instructions" should read "the first instructions"

Signed and Sealed this
Fourteenth Day of January, 2020

Andrei Iancu
*Director of the United States Patent and Trademark Office*